(12) United States Patent
Neumann

(10) Patent No.: US 11,830,588 B2
(45) Date of Patent: Nov. 28, 2023

(54) METHODS AND SYSTEMS FOR A PHYSIOLOGICALLY INFORMED VIRTUAL SUPPORT NETWORK

(71) Applicant: KPN Innovations, LLC, Lakewood, CO (US)

(72) Inventor: Kenneth Neumann, Lakewood, CO (US)

(73) Assignee: KPN Innovations, LLC, Lakewood, CO (US)

( * ) Notice: Subject to any disclaimer, the term of this patent is extended or adjusted under 35 U.S.C. 154(b) by 357 days.

(21) Appl. No.: 16/863,113

(22) Filed: Apr. 30, 2020

(65) Prior Publication Data

US 2021/0343376 A1    Nov. 4, 2021

(51) Int. Cl.
*G16H 80/00*     (2018.01)
*G06Q 50/00*     (2012.01)
*G16H 10/20*     (2018.01)
*G06N 20/00*     (2019.01)

(52) U.S. Cl.
CPC ............. *G16H 10/20* (2018.01); *G06N 20/00* (2019.01); *G06Q 50/01* (2013.01); *G16H 80/00* (2018.01)

(58) Field of Classification Search
CPC ......... G06Q 50/01; G16H 10/60; G16H 80/00
See application file for complete search history.

(56) References Cited

U.S. PATENT DOCUMENTS

| | | | |
|---|---|---|---|
| 9,992,292 B2 | 6/2018 | Gunnarsson et al. | |
| 2003/0061072 A1* | 3/2003 | Baker | G16H 10/20 705/3 |
| 2005/0117527 A1 | 6/2005 | Williams | |
| 2006/0205564 A1 | 9/2006 | Peterson | |
| 2009/0070378 A1* | 3/2009 | Cho | G16H 50/70 |
| 2010/0205542 A1 | 8/2010 | Walman | |
| 2011/0029622 A1* | 2/2011 | Walker | G06Q 10/107 709/206 |
| 2011/0125844 A1* | 5/2011 | Collier | H04W 4/38 709/204 |

(Continued)

FOREIGN PATENT DOCUMENTS

KR    20120076564 A  *  7/2012

*Primary Examiner* — Karen A Hranek
(74) *Attorney, Agent, or Firm* — CALDWELL INTELLECTUAL PROPERTY LAW

(57) ABSTRACT

A system for a physiologically informed virtual support network includes a computing device a support module operating on the computing device, the support module configured to receive a biological extraction related to a user, wherein the biological extraction comprises an element of user physiological data, generate a request for the user to join a support network as a function of the biological extraction, identify a support network for the user from a plurality of support networks, as a function of the biological extraction; and display to the user on the computing device, the identified support network, and a machine-learning module operating on the computing device, the machine-learning module configured to assess a membership of the plurality of support networks, organize member participants of the plurality of support networks utilizing a first machine-learning process and assign member participants to the plurality of support networks as a function of the first machine-learning process.

20 Claims, 5 Drawing Sheets

(56) References Cited

U.S. PATENT DOCUMENTS

| | | | |
|---|---|---|---|
| 2011/0153740 A1* | 6/2011 | Smith | H04L 67/20 |
| | | | 709/204 |
| 2012/0042013 A1* | 2/2012 | Roman | G06Q 10/101 |
| | | | 709/204 |
| 2012/0244504 A1* | 9/2012 | Wasserman | G09B 19/00 |
| | | | 434/238 |
| 2012/0278101 A1* | 11/2012 | Homchowdhury | H04L 63/20 |
| | | | 705/3 |
| 2012/0308975 A1 | 12/2012 | Hsiao et al. | |
| 2013/0013340 A1 | 1/2013 | Hsiao et al. | |
| 2013/0035946 A1* | 2/2013 | Ratan | G16H 40/67 |
| | | | 705/2 |
| 2014/0101066 A1 | 4/2014 | Stollmeyer et al. | |
| 2014/0142397 A1 | 5/2014 | Bedrosian et al. | |
| 2014/0310013 A1* | 10/2014 | Ram | G16H 50/20 |
| | | | 705/2 |
| 2014/0330576 A1* | 11/2014 | Bauer | G16H 40/67 |
| | | | 705/2 |
| 2015/0019273 A1* | 1/2015 | Grosz | G06Q 10/02 |
| | | | 705/5 |
| 2015/0052160 A1* | 2/2015 | Hussam | G06F 16/245 |
| | | | 707/758 |
| 2015/0281384 A1* | 10/2015 | Gunnarsson | G16H 40/67 |
| | | | 709/204 |
| 2017/0262587 A1* | 9/2017 | Agarwal | G16H 50/20 |
| 2018/0107800 A1* | 4/2018 | Cerrone | G16H 10/60 |
| 2019/0189285 A1* | 6/2019 | Lowet | G16H 50/30 |
| 2020/0342545 A1* | 10/2020 | Dobson | G16H 40/20 |
| 2020/0351234 A1* | 11/2020 | Gaon | G06Q 50/01 |

\* cited by examiner

METHODS AND SYSTEMS FOR A PHYSIOLOGICALLY INFORMED VIRTUAL SUPPORT NETWORK

FIELD OF THE INVENTION

The present invention generally relates to the field of artificial intelligence. In particular, the present invention is directed to a system for a physiologically informed virtual support network.

BACKGROUND

Identifying support networks best suited for each individual member can be challenging. Frequently, member preferences can misalign with preferences of support networks. There remains to be seen a way to personalize selection of support networks.

SUMMARY OF THE DISCLOSURE

In an aspect, a system for a physiologically informed virtual support network includes a computing device, a support module operating on the computing device, the support module configured to receive a biological extraction related to a user, the biological extraction comprising an element of user physiological data, generate a request for the user to join a support network as a function of the biological extraction, identify a support network for the user from a plurality of support networks, as a function of the biological extraction and display to the user on the computing device, the identified support network. The system includes a machine-learning module operating on the computing device, the machine-learning module configured to assess a membership of the plurality of support networks, organize member participants of the plurality of support networks utilizing a first machine-learning process, and assign member participants to the plurality of support networks as a function of the first machine-learning process.

In an aspect, a method of a physiologically informed virtual support network includes generating, by a computing device, a request for a user to join a support network as a function of a biological extraction related to a user; identifying by the computing device, a support network for the user from a plurality of support networks, as a function of the biological extraction, displaying to the user on the computing device, the identified support network, assessing by the computing device, a membership of the plurality of support networks, organizing by the computing device, the membership of the plurality of support networks utilizing a first machine-learning process, and assigning by the computing device, the membership to the plurality of support networks as a function of the first machine-learning process.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for a physiologically informed virtual support network. In an embodiment, a biological extraction containing an element of physiological data is utilized to inform selection of a virtual support network. Selection can also be customized utilizing responses generated by a user containing information related to user participation and engagement, as well as goals for joining a support network.

Figure 1:
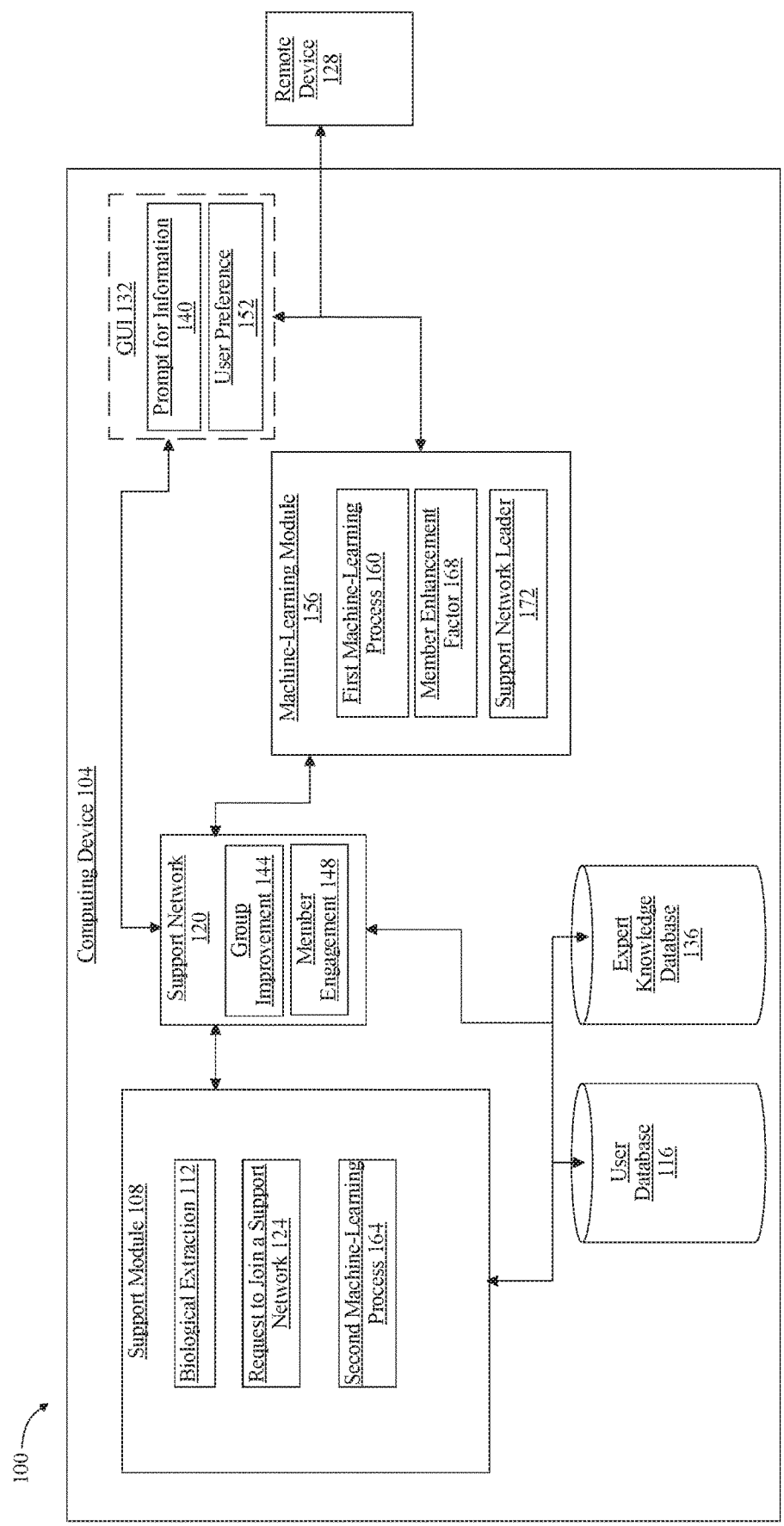
FIG. 1 is a block diagram illustrating an exemplary embodiment of a system for a physiologically informed virtual support network.

Referring now to FIG. 1, an exemplary embodiment of a system 100 for a physiologically informed virtual support network is illustrated. System 100 includes a computing device 104. Computing device 104 may include any computing device 104 as described in this disclosure, including without limitation a microcontroller, microprocessor, digital signal processor (DSP) and/or system on a chip (SoC) as described in this disclosure. Computing device 104 may include, be included in, and/or communicate with a mobile device such as a mobile telephone or smartphone. Computing device 104 may include a single computing device 104 operating independently or may include two or more computing device 104 operating in concert, in parallel, sequentially or the like; two or more computing devices 104 may be included together in a single computing device 104 or in two or more computing devices 104. Computing device 104 may interface or communicate with one or more additional devices as described below in further detail via a network interface device. Network interface device may be utilized for connecting computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices 104, and any combinations thereof. A network may employ a wired and/or a wireless mode of communication. In general, any network topology may be used. Information (e.g., data, software etc.) may be communicated to and/or from a computer and/or a computing device 104. Computing device 104 may include but is not limited to, for example, a computing device 104 or cluster of computing devices 104 in a first location and a second computing device 104 or cluster of computing devices 104 in a second location. Computing device 104 may include one or more computing devices 104 dedicated to data storage, security, distribution of traffic for load balancing, and the like. Computing device 104 may distribute one or more computing tasks as described below across a plurality of computing devices 104 of computing device 104, which may operate in parallel, in series, redundantly, or in any other manner used for distribution of tasks or memory between computing devices 104. Computing device 104 may be implemented using a "shared nothing" architecture in which data is cached at the worker, in an embodiment, this may enable scalability of system 100 and/or computing device 104.

Continuing to refer to FIG. 1, computing device 104 may be designed and/or configured to perform any method, method step, or sequence of method steps in any embodiment described in this disclosure, in any order and with any degree of repetition. For instance, computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With continued reference to FIG. 1, computing device 104 includes a support module 108. Support module 108 may be implemented as any hardware and/or software module. Support module 108 is designed and configured to receive a biological extraction 112 pertaining to a user. A "biological extraction," as used in this disclosure, is an element of data including at least an element of user physiological data. As used in this disclosure, "physiological data" is any data indicative of a person's physiological state; physiological state may be evaluated with regard to one or more measures of health of a person's body, one or more systems within a person's body such as a circulatory system, a digestive system, a nervous system, or the like, one or more organs within a person's body, and/or any other subdivision of a person's body useful for diagnostic or prognostic purposes. For instance, and without limitation, a particular set of biomarkers, test results, and/or biochemical information may be recognized in a given medical field as useful for identifying various disease conditions or prognoses within a relevant field. As a non-limiting example, and without limitation, physiological data describing red blood cells, such as red blood cell count, hemoglobin levels, hematocrit, mean corpuscular volume, mean corpuscular hemoglobin, and/or mean corpuscular hemoglobin concentration may be recognized as useful for identifying various conditions such as dehydration, high testosterone, nutrient deficiencies, kidney dysfunction, chronic inflammation, anemia, and/or blood loss.

With continued reference to FIG. 1, physiological state data may include, without limitation, hematological data, such as red blood cell count, which may include a total number of red blood cells in a person's blood and/or in a blood sample, hemoglobin levels, hematocrit representing a percentage of blood in a person and/or sample that is composed of red blood cells, mean corpuscular volume, which may be an estimate of the average red blood cell size, mean corpuscular hemoglobin, which may measure average weight of hemoglobin per red blood cell, mean corpuscular hemoglobin concentration, which may measure an average concentration of hemoglobin in red blood cells, platelet count, mean platelet volume which may measure the average size of platelets, red blood cell distribution width, which measures variation in red blood cell size, absolute neutrophils, which measures the number of neutrophil white blood cells, absolute quantities of lymphocytes such as B-cells, T-cells, Natural Killer Cells, and the like, absolute numbers of monocytes including macrophage precursors, absolute numbers of eosinophils, and/or absolute counts of basophils. Physiological state data may include, without limitation, immune function data such as Interleukine-6 (IL-6), TNF-alpha, systemic inflammatory cytokines, and the like.

Continuing to refer to FIG. 1, physiological state data may include, without limitation, data describing blood-born lipids, including total cholesterol levels, high-density lipoprotein (HDL) cholesterol levels, low-density lipoprotein (LDL) cholesterol levels, very low-density lipoprotein (VLDL) cholesterol levels, levels of triglycerides, and/or any other quantity of any blood-born lipid or lipid-containing substance. Physiological state data may include measures of glucose metabolism such as fasting glucose levels and/or hemoglobin A1-C(HbA1c) levels. Physiological state data may include, without limitation, one or more measures associated with endocrine function, such as without limitation, quantities of dehydroepiandrosterone (DHEAS), DHEA-Sulfate, quantities of cortisol, ratio of DHEAS to cortisol, quantities of testosterone quantities of estrogen, quantities of growth hormone (GH), insulin-like growth factor 1 (IGF-1), quantities of adipokines such as adiponectin, leptin, and/or ghrelin, quantities of somatostatin, progesterone, or the like. Physiological state data may include measures of estimated glomerular filtration rate (eGFR). Physiological state data may include quantities of C-reactive protein, estradiol, ferritin, folate, homocysteine, prostate-specific Ag, thyroid-stimulating hormone, vitamin D, 25 hydroxy, blood urea nitrogen, creatinine, sodium, potassium, chloride, carbon dioxide, uric acid, albumin, globulin, calcium, phosphorus, alkaline phosphatase, alanine amino transferase, aspartate amino transferase, lactate dehydrogenase (LDH), bilirubin, gamma-glutamyl transferase (GGT), iron, and/or total iron binding capacity (TIBC), or the like. Physiological state data may include antinuclear antibody levels. Physiological state data may include aluminum levels. Physiological state data may include arsenic levels. Physiological state data may include levels of fibrinogen, plasma cystatin C, and/or brain natriuretic peptide.

Continuing to refer to FIG. 1, physiological state data may include measures of lung function such as forced expiratory volume, one second (FEV-1) which measures how much air can be exhaled in one second following a deep inhalation, forced vital capacity (FVC), which measures the volume of air that may be contained in the lungs. Physiological state data may include a measurement blood pressure, including without limitation systolic and diastolic blood pressure. Physiological state data may include a measure of waist circumference. Physiological state data may include body mass index (BMI). Physiological state data may include one or more measures of bone mass and/or density such as dual-energy x-ray absorptiometry. Physiological state data may include one or more measures of muscle mass. Physiological state data may include one or more measures of physical capability such as without limitation measures of grip strength, evaluations of standing balance, evaluations of gait speed, pegboard tests, timed up and go tests, and/or chair rising tests.

Still viewing FIG. 1, physiological state data may include one or more measures of cognitive function, including without limitation Rey auditory verbal learning test results, California verbal learning test results, NIH toolbox picture sequence memory test, Digital symbol coding evaluations, and/or Verbal fluency evaluations. Physiological state data may include one or more evaluations of sensory ability, including measures of audition, vision, olfaction, gustation, vestibular function and pain.

Continuing to refer to FIG. 1, physiological state data may include psychological data. Psychological data may include any data generated using psychological, neuro-psychological, and/or cognitive evaluations, as well as diagnostic screening tests, personality tests, personal compatibility tests, or the like; such data may include, without limitation, numerical score data entered by an evaluating professional and/or by a subject performing a self-test such as a computerized questionnaire. Psychological data may include textual, video, or image data describing testing, analysis, and/or conclusions entered by a medical professional such as without limitation a psychologist, psychiatrist, psychotherapist, social worker, a medical doctor, or the like. Psychological data may include data gathered from user interactions with persons, documents, and/or computing devices 104; for instance, user patterns of purchases, including electronic purchases, communication such as via chat-rooms or the like, any textual, image, video, and/or data produced by the subject, any textual image, video and/or other data depicting and/or describing the subject, or the like. Any psychological data and/or data used to generate psychological data may be analyzed using machine-learning and/or language processing module as described in this disclosure. As a non-limiting example, biological extraction 112 may include a psychological profile; the psychological profile may be obtained utilizing a questionnaire performed by the user.

Still referring to FIG. 1, physiological state data may include genomic data, including deoxyribonucleic acid (DNA) samples and/or sequences, such as without limitation DNA sequences or other genetic sequences contained in one or more chromosomes in human cells. Genomic data may include, without limitation, ribonucleic acid (RNA) samples and/or sequences, such as samples and/or sequences of messenger RNA (mRNA) or the like taken from human cells. Genetic data may include telomere lengths. Genomic data may include epigenetic data including data describing one or more states of methylation of genetic material. Physiological state data may include proteomic data, which as used herein is data describing all proteins produced and/or modified by an organism, colony of organisms, or system of organisms, and/or a subset thereof. Physiological state data may include data concerning a microbiome of a person, which as used herein includes any data describing any microorganism and/or combination of microorganisms living on or within a person, including without limitation biomarkers, genomic data, proteomic data, and/or any other metabolic or biochemical data useful for analysis of the effect of such microorganisms on other physiological state data of a person, as described in further detail below.

With continuing reference to FIG. 1, physiological state data may include one or more user-entered descriptions of a person's physiological state. One or more user-entered descriptions may include, without limitation, user descriptions of symptoms, which may include without limitation current or past physical, psychological, perceptual, and/or neurological symptoms, user descriptions of current or past physical, emotional, and/or psychological problems and/or concerns, user descriptions of past or current treatments, including therapies, nutritional regimens, exercise regimens, pharmaceuticals or the like, or any other user-entered data that a user may provide to a medical professional when seeking treatment and/or evaluation, and/or in response to medical intake papers, questionnaires, questions from medical professionals, or the like. Physiological state data may include any physiological state data, as described above, describing any multicellular organism living in or on a person including any parasitic and/or symbiotic organisms living in or on the persons; non-limiting examples may include mites, nematodes, flatworms, or the like. Examples of physiological state data described in this disclosure are presented for illustrative purposes only and are not meant to be exhaustive.

With continued reference to FIG. 1, physiological data may include, without limitation any result of any medical test, physiological assessment, cognitive assessment, psychological assessment, or the like. System 100 may receive at least a physiological data from one or more other devices after performance; system 100 may alternatively or additionally perform one or more assessments and/or tests to obtain at least a physiological data, and/or one or more portions thereof, on system 100. For instance, at least physiological data may include or more entries by a user in a form or similar graphical user interface object; one or more entries may include, without limitation, user responses to questions on a psychological, behavioral, personality, or cognitive test. For instance, at least a server may present to user a set of assessment questions designed or intended to evaluate a current state of mind of the user, a current psychological state of the user, a personality trait of the user, or the like; at least a server may provide user-entered responses to such questions directly as at least a physiological data and/or may perform one or more calculations or other algorithms to derive a score or other result of an assessment as specified by one or more testing protocols, such as automated calculation of a Stanford-Binet and/or Wechsler scale for IQ testing, a personality test scoring such as a Myers-Briggs test protocol, or other assessments that may occur to persons skilled in the art upon reviewing the entirety of this disclosure.

With continued reference to FIG. 1, assessment and/or self-assessment data, and/or automated or other assessment results, obtained from a third-party device; third-party device may include, without limitation, a server or other device (not shown) that performs automated cognitive, psychological, behavioral, personality, or other assessments. Third-party device may include a device operated by an informed advisor. An informed advisor may include any medical professional who may assist and/or participate in the medical treatment of a user. An informed advisor may include a medical doctor, nurse, physician assistant, pharmacist, yoga instructor, nutritionist, spiritual healer, meditation teacher, fitness coach, health coach, life coach, and the like.

With continued reference to FIG. 1, physiological data may include data describing one or more test results, including results of mobility tests, stress tests, dexterity tests, endocrinal tests, genetic tests, and/or electromyographic tests, biopsies, radiological tests, genetic tests, and/or sensory tests. Persons skilled in the art, upon reviewing the entirety of this disclosure, will be aware of various additional examples of at least a physiological sample consistent with this disclosure.

With continued reference to FIG. 1, physiological data may include one or more user body measurements. A "user body measurement" as used in this disclosure, includes a measurable indicator of the severity, absence, and/or presence of a disease state. A "disease state" as used in this disclosure, includes any harmful deviation from the normal structural and/or function state of a human being. A disease state may include any medical condition and may be associated with specific symptoms and signs. A disease state may be classified into different types including infectious diseases, deficiency diseases, hereditary diseases, and/or physiological diseases. For instance and without limitation, internal dysfunction of the immune system may produce a variety of different diseases including immunodeficiency, hypersensitivity, allergies, and/or autoimmune disorders.

With continued reference to FIG. 1, user body measurements may be related to particular dimensions of the human body. A "dimension of the human body" as used in this disclosure, includes one or more functional body systems that are impaired by disease in a human body and/or animal body. Functional body systems may include one or more body systems recognized as attributing to root causes of disease by functional medicine practitioners and experts. A "root cause" as used in this disclosure, includes any chain of causation describing underlying reasons for a particular disease state and/or medical condition instead of focusing solely on symptomatology reversal. Root cause may include chains of causation developed by functional medicine practices that may focus on disease causation and reversal. For instance and without limitation, a medical condition such as diabetes may include a chain of causation that does not include solely impaired sugar metabolism but that also includes impaired hormone systems including insulin resistance, high cortisol, less than optimal thyroid production, and low sex hormones. Diabetes may include further chains of causation that include inflammation, poor diet, delayed food allergies, leaky gut, oxidative stress, damage to cell membranes, and dysbiosis. Dimensions of the human body may include but are not limited to epigenetics, gut-wall, microbiome, nutrients, genetics, and/or metabolism.

With continued reference to FIG. 1, epigenetic, as used herein, includes any user body measurements describing changes to a genome that do not involve corresponding changes in nucleotide sequence. Epigenetic body measurement may include data describing any heritable phenotypic. Phenotype, as used herein, include any observable trait of a user including morphology, physical form, and structure. Phenotype may include a user's biochemical and physiological properties, behavior, and products of behavior. Behavioral phenotypes may include cognitive, personality, and behavior patterns. This may include effects on cellular and physiological phenotypic traits that may occur due to external or environmental factors. For example, DNA methylation and histone modification may alter phenotypic expression of genes without altering underlying DNA sequence. Epigenetic body measurements may include data describing one or more states of methylation of genetic material.

With continued reference to FIG. 1, gut-wall, as used herein, includes the space surrounding the lumen of the gastrointestinal tract that is composed of four layers including the mucosa, submucosa, muscular layer, and serosa. The mucosa contains the gut epithelium that is composed of goblet cells that function to secrete mucus, which aids in lubricating the passage of food throughout the digestive tract. The goblet cells also aid in protecting the intestinal wall from destruction by digestive enzymes. The mucosa includes villi or folds of the mucosa located in the small intestine that increase the surface area of the intestine. The villi contain a lacteal, that is a vessel connected to the lymph system that aids in removal of lipids and tissue fluids. Villi may contain microvilli that increase the surface area over which absorption can take place. The large intestine lack villi and instead a flat surface containing goblet cells are present.

With continued reference to FIG. 1, gut-wall includes the submucosa, which contains nerves, blood vessels, and elastic fibers containing collagen. Elastic fibers contained within the submucosa aid in stretching the gastrointestinal tract with increased capacity while also maintaining the shape of the intestine. Gut-wall includes muscular layer which contains smooth muscle that aids in peristalsis and the movement of digested material out of and along the gut. Gut-wall includes the serosa which is composed of connective tissue and coated in mucus to prevent friction damage from the intestine rubbing against other tissue. Mesenteries are also found in the serosa and suspend the intestine in the abdominal cavity to stop it from being disturbed when a person is physically active.

With continued reference to FIG. 1, gut-wall body measurement may include data describing one or more test results including results of gut-wall function, gut-wall integrity, gut-wall strength, gut-wall absorption, gut-wall permeability, intestinal absorption, gut-wall barrier function, gut-wall absorption of bacteria, gut-wall malabsorption, gut-wall gastrointestinal imbalances and the like.

With continued reference to FIG. 1, gut-wall body measurement may include any data describing blood test results of creatinine levels, lactulose levels, zonulin levels, and mannitol levels. Gut-wall body measurement may include blood test results of specific gut-wall body measurements including d-lactate, endotoxin lipopolysaccharide (LPS) Gut-wall body measurement may include data breath tests measuring lactulose, hydrogen, methane, lactose, and the like. Gut-wall body measurement may include blood test results describing blood chemistry levels of albumin, bilirubin, complete blood count, electrolytes, minerals, sodium, potassium, calcium, glucose, blood clotting factors, With continued reference to FIG. 1, gut-wall body measurement may include one or more stool test results describing presence or absence of parasites, firmicutes, Bacteroidetes, absorption, inflammation, food sensitivities. Stool test results may describe presence, absence, and/or measurement of acetate, aerobic bacterial cultures, anerobic bacterial cultures, fecal short chain fatty acids, beta-glucuronidase, cholesterol, chymotrypsin, fecal color, *cryptosporidium* EIA, *Entamoeba histolytica*, fecal lactoferrin, *Giardia lamblia* EIA, long chain fatty acids, meat fibers and vegetable fibers, mucus, occult blood, parasite identification, phospholipids, propionate, putrefactive short chain fatty acids, total fecal fat, triglycerides, yeast culture, n-butyrate, pH and the like.

With continued reference to FIG. 1, gut-wall body measurement may include one or more stool test results describing presence, absence, and/or measurement of microorganisms including bacteria, archaea, fungi, protozoa, algae, viruses, parasites, worms, and the like. Stool test results may contain species such as *Bifidobacterium* species, *campylobacter* species, *Clostridium difficile, cryptosporidium* species, *Cyclospora cayetanensis, Cryptosporidium* EIA, *Dientamoeba fragilis, Entamoeba histolytica, Escherichia coli, Entamoeba histolytica, Giardia, H. pylori, Candida albicans, Lactobacillus* species, worms, macroscopic worms, mycology, protozoa, Shiga toxin *E. coli*, and the like.

With continued reference to FIG. 1, gut-wall body measurement may include one or more microscopic ova exam results, microscopic parasite exam results, protozoan polymerase chain reaction test results and the like. Gut-wall body measurement may include enzyme-linked immunosorbent assay (ELISA) test results describing immunoglobulin G (Ig G) food antibody results, immunoglobulin E (Ig E) food antibody results, Ig E mold results, IgG spice and herb results. Gut-wall body measurement may include measurements of calprotectin, eosinophil protein x (EPX), stool weight, pancreatic elastase, total urine volume, blood creatinine levels, blood lactulose levels, blood mannitol levels.

With continued reference to FIG. 1, gut-wall body measurement may include one or more elements of data describing one or more procedures examining gut including for example colonoscopy, endoscopy, large and small molecule challenge and subsequent urinary recovery using large molecules such as lactulose, polyethylene glycol-3350, and small molecules such as mannitol, L-rhamnose, polyethyleneglycol-400. Gut-wall body measurement may include data describing one or more images such as x-ray, MRI, CT scan, ultrasound, standard barium follow-through examination, barium enema, barium with contract, MRI fluoroscopy, positron emission tomography 9PET), diffusion-weighted MRI imaging, and the like.

With continued reference to FIG. 1, microbiome, as used herein, includes ecological community of commensal, symbiotic, and pathogenic microorganisms that reside on or within any of a number of human tissues and biofluids. For example, human tissues and biofluids may include the skin, mammary glands, placenta, seminal fluid, uterus, vagina, ovarian follicles, lung, saliva, oral mucosa, conjunctiva, biliary, and gastrointestinal tracts. Microbiome may include for example, bacteria, archaea, protists, fungi, and viruses. Microbiome may include commensal organisms that exist within a human being without causing harm or disease. Microbiome may include organisms that are not harmful but rather harm the human when they produce toxic metabolites such as trimethylamine. Microbiome may include pathogenic organisms that cause host damage through virulence factors such as producing toxic by-products. Microbiome may include populations of microbes such as bacteria and yeasts that may inhabit the skin and mucosal surfaces in various parts of the body. Bacteria may include for example Firmicutes species, Bacteroidetes species, Proteobacteria species, Verrumicrobia species, Actinobacteria species, Fusobacteria species, Cyanobacteria species and the like. Archaea may include methanogens such as *Methanobrevibacter* smithies' and *Methanosphaera stadtmanae*. Fungi may include *Candida* species and *Malassezia* species. Viruses may include bacteriophages. Microbiome species may vary in different locations throughout the body. For example, the genitourinary system may contain a high prevalence of *Lactobacillus* species while the gastrointestinal tract may contain a high prevalence of *Bifidobacterium* species while the lung may contain a high prevalence of *Streptococcus* and *Staphylococcus* species.

With continued reference to FIG. 1, microbiome body measurement may include one or more stool test results describing presence, absence, and/or measurement of microorganisms including bacteria, archaea, fungi, protozoa, algae, viruses, parasites, worms, and the like. Stool test results may contain species such as Ackerman's *muciniphila, Anaerotruncus colihominis*, bacteriology, *Bacteroides* vulgates', *Bacteroides-Prevotella, Barnesiella* species, *Bifidobacterium longarm, Bifidobacterium* species, *Butyrivbrio crossotus, Clostridium* species, *Collinsella aerofaciens*, fecal color, fecal consistency, *Coprococcus eutactus, Desulfovibrio piger, Escherichia coli, Faecalibacterium prausnitzii*, Fecal occult blood, Firmicutes to Bacteroidetes ratio, *Fusobacterium* species, *Lactobacillus* species, *Methanobrevibacter smithii*, yeast minimum inhibitory concentration, bacteria minimum inhibitory concentration, yeast mycology, fungi mycology, *Odoribacter* species, *Oxalobacter formigenes*, parasitology, *Prevotella* species, *Pseudoflavonifractor* species, *Roseburia* species, *Ruminococcus* species, *Veillonella* species and the like.

With continued reference to FIG. 1, microbiome body measurement may include one or more stool tests results that identify all microorganisms living a user's gut including bacteria, viruses, archaea, yeast, fungi, parasites, and bacteriophages. Microbiome body measurement may include DNA and RNA sequences from live microorganisms that may impact a user's health. Microbiome body measurement may include high resolution of both species and strains of all microorganisms. Microbiome body measurement may include data describing current microbe activity. Microbiome body measurement may include expression of levels of active microbial gene functions. Microbiome body measurement may include descriptions of sources of disease-causing microorganisms, such as viruses found in the gastrointestinal tract such as raspberry bushy swarf virus from consuming contaminated raspberries or Pepino mosaic virus from consuming contaminated tomatoes.

With continued reference to FIG. 1, microbiome body measurement may include one or more blood test results that identify metabolites produced by microorganisms. Metabolites may include for example, indole-3-propionic acid, indole-3-lactic acid, indole-3-acetic acid, tryptophan, serotonin, kynurenine, total indoxyl sulfate, tyrosine, xanthine, 3-methylxanthine, uric acid, and the like.

With continued reference to FIG. 1, microbiome body measurement may include one or more breath test results that identify certain strains of microorganisms that may be present in certain areas of a user's body. This may include for example, lactose intolerance breath tests, methane-based breath tests, hydrogen-based breath tests, fructose-based breath tests, *Helicobacter pylori* breath test, fructose intolerance breath test, bacterial overgrowth syndrome breath tests and the like.

With continued reference to FIG. 1, microbiome body measurement may include one or more urinary analysis results for certain microbial strains present in urine. This may include for example, urinalysis that examines urine specific gravity, urine cytology, urine sodium, urine culture, urinary calcium, urinary hematuria, urinary glucose levels, urinary acidity, urinary protein, urinary nitrites, bilirubin, red blood cell urinalysis, and the like.

With continued reference to FIG. 1, nutrient as used herein, includes any substance required by the human body to function. Nutrients may include carbohydrates, protein, lipids, vitamins, minerals, antioxidants, fatty acids, amino acids, and the like. Nutrients may include for example vitamins such as thiamine, riboflavin, niacin, pantothenic acid, pyridoxine, biotin, folate, cobalamin, Vitamin C, Vitamin A, Vitamin D, Vitamin E, and Vitamin K. Nutrients may include for example minerals such as sodium, chloride, potassium, calcium, phosphorous, magnesium, sulfur, iron, zinc, iodine, selenium, copper, manganese, fluoride, chromium, molybdenum, nickel, aluminum, silicon, vanadium, arsenic, and boron.

With continued reference to FIG. 1, nutrients may include extracellular nutrients that are free floating in blood and exist outside of cells. Extracellular nutrients may be located in serum. Nutrients may include intracellular nutrients which may be absorbed by cells including white blood cells and red blood cells.

With continued reference to FIG. 1, nutrient body measurement may include one or more blood test results that identify extracellular and intracellular levels of nutrients. Nutrient body measurement may include blood test results that identify serum, white blood cell, and red blood cell levels of nutrients. For example, nutrient body measurement may include serum, white blood cell, and red blood cell levels of micronutrients such as Vitamin A, Vitamin B1, Vitamin B2, Vitamin B3, Vitamin B6, Vitamin B12, Vitamin B5, Vitamin C, Vitamin D, Vitamin E, Vitamin K1, Vitamin K2, and folate.

With continued reference to FIG. 1, nutrient body measurement may include one or more blood test results that identify serum, white blood cell and red blood cell levels of nutrients such as calcium, manganese, zinc, copper, chromium, iron, magnesium, copper to zinc ratio, choline, inositol, carnitine, methylmalonic acid (MMA), sodium, potassium, asparagine, glutamine, serine, coenzyme q10, cysteine, alpha lipoic acid, glutathione, selenium, eicosapentaenoic acid (EPA), docosahexaenoic acid (DHA), docosapentaenoic acid (DPA), total omega-3, lauric acid, arachidonic acid, oleic acid, total omega 6, and omega 3 index.

With continued reference to FIG. 1, nutrient body measurement may include one or more salivary test results that identify levels of nutrients including any of the nutrients as described herein. Nutrient body measurement may include hair analysis of levels of nutrients including any of the nutrients as described herein.

With continued reference to FIG. 1, genetic as used herein, includes any inherited trait. Inherited traits may include genetic material contained with DNA including for example, nucleotides. Nucleotides include adenine (A), cytosine (C), guanine (G), and thymine (T). Genetic information may be contained within the specific sequence of an individual's nucleotides and sequence throughout a gene or DNA chain. Genetics may include how a particular genetic sequence may contribute to a tendency to develop a certain disease such as cancer or Alzheimer's disease.

With continued reference to FIG. 1, genetic body measurement may include one or more results from one or more blood tests, hair tests, skin tests, urine, amniotic fluid, buccal swabs and/or tissue test to identify a user's particular sequence of nucleotides, genes, chromosomes, and/or proteins. Genetic body measurement may include tests that example genetic changes that may lead to genetic disorders. Genetic body measurement may detect genetic changes such as deletion of genetic material or pieces of chromosomes that may cause Duchenne Muscular Dystrophy. Genetic body measurement may detect genetic changes such as insertion of genetic material into DNA or a gene such as the BRCA1 gene that is associated with an increased risk of breast and ovarian cancer due to insertion of 2 extra nucleotides. Genetic body measurement may include a genetic change such as a genetic substitution from a piece of genetic material that replaces another as seen with sickle cell anemia where one nucleotide is substituted for another. Genetic body measurement may detect a genetic change such as a duplication when extra genetic material is duplicated one or more times within a person's genome such as with Charcot-Marie Tooth disease type 1. Genetic body measurement may include a genetic change such as an amplification when there is more than a normal number of copies of a gene in a cell such as HER2 amplification in cancer cells. Genetic body measurement may include a genetic change such as a chromosomal translocation when pieces of chromosomes break off and reattach to another chromosome such as with the BCR-ABL1 gene sequence that is formed when pieces of chromosome 9 and chromosome 22 break off and switch places. Genetic body measurement may include a genetic change such as an inversion when one chromosome experiences two breaks and the middle piece is flipped or inverted before reattaching. Genetic body measurement may include a repeat such as when regions of DNA contain a sequence of nucleotides that repeat a number of times such as for example in Huntington's disease or Fragile X syndrome. Genetic body measurement may include a genetic change such as a trisomy when there are three chromosomes instead of the usual pair as seen with Down syndrome with a trisomy of chromosome 21, Edwards syndrome with a trisomy at chromosome 18 or Patau syndrome with a trisomy at chromosome 13. Genetic body measurement may include a genetic change such as monosomy such as when there is an absence of a chromosome instead of a pair, such as in Turner syndrome.

With continued reference to FIG. 1, genetic body measurement may include an analysis of COMT gene that is responsible for producing enzymes that metabolize neurotransmitters. Genetic body measurement may include an analysis of DRD2 gene that produces dopamine receptors in the brain. Genetic body measurement may include an analysis of ADRA2B gene that produces receptors for noradrenaline. Genetic body measurement may include an analysis of 5-HTTLPR gene that produces receptors for serotonin. Genetic body measurement may include an analysis of BDNF gene that produces brain derived neurotrophic factor. Genetic body measurement may include an analysis of 9p21 gene that is associated with cardiovascular disease risk. Genetic body measurement may include an analysis of APOE gene that is involved in the transportation of blood lipids such as cholesterol. Genetic body measurement may include an analysis of NOS3 gene that is involved in producing enzymes involved in regulating vasodilation and vasoconstriction of blood vessels.

With continued reference to FIG. 1, genetic body measurement may include ACE gene that is involved in producing enzymes that regulate blood pressure. Genetic body measurement may include SLCO1B1 gene that directs pharmaceutical compounds such as statins into cells. Genetic body measurement may include FUT2 gene that produces enzymes that aid in absorption of Vitamin B12 from digestive tract. Genetic body measurement may include MTHFR gene that is responsible for producing enzymes that aid in metabolism and utilization of Vitamin B9 or folate. Genetic body measurement may include SHMT1 gene that aids in production and utilization of Vitamin B9 or folate. Genetic body measurement may include MTRR gene that produces enzymes that aid in metabolism and utilization of Vitamin B12. Genetic body measurement may include MTR gene that produces enzymes that aid in metabolism and utilization of Vitamin B12. Genetic body measurement may include FTO gene that aids in feelings of satiety or fullness after eating. Genetic body measurement may include MC4R gene that aids in producing hunger cues and hunger triggers. Genetic body measurement may include APOA2 gene that directs body to produce ApoA2 thereby affecting absorption of saturated fats. Genetic body measurement may include UCP1 gene that aids in controlling metabolic rate and thermoregulation of body. Genetic body measurement may include TCF7L2 gene that regulates insulin secretion. Genetic body measurement may include AMY1 gene that aids in digestion of starchy foods. Genetic body measurement may include MCM6 gene that controls production of lactase enzyme that aids in digesting lactose found in dairy products. Genetic body measurement may include BCMO1 gene that aids in producing enzymes that aid in metabolism and activation of Vitamin A. Genetic body measurement may include SLC23A1 gene that produce and transport Vitamin C. Genetic body measurement may include CYP2R1 gene that produce enzymes involved in production and activation of Vitamin D. Genetic body measurement may include GC gene that produce and transport Vitamin D. Genetic body measurement may include CYP1A2 gene that aid in metabolism and elimination of caffeine. Genetic body measurement may include CYP17A1 gene that produce enzymes that convert progesterone into androgens such as androstenedione, androstendiol, dehydroepiandrosterone, and testosterone.

With continued reference to FIG. 1, genetic body measurement may include CYP19A1 gene that produce enzymes that convert androgens such as androstenedione and testosterone into estrogens including estradiol and estrone. Genetic body measurement may include SRD5A2 gene that aids in production of enzymes that convert testosterone into dihydrotestosterone. Genetic body measurement may include UFT2B17 gene that produces enzymes that metabolize testosterone and dihydrotestosterone. Genetic body measurement may include CYP1A1 gene that produces enzymes that metabolize estrogens into 2 hydroxy-estrogen. Genetic body measurement may include CYP1B1 gene that produces enzymes that metabolize estrogens into 4 hydroxy-estrogen. Genetic body measurement may include CYP3A4 gene that produces enzymes that metabolize estrogen into 16 hydroxy-estrogen. Genetic body measurement may include COMT gene that produces enzymes that metabolize 2 hydroxy-estrogen and 4 hydroxy-estrogen into methoxy estrogen. Genetic body measurement may include GSTT1 gene that produces enzymes that eliminate toxic by-products generated from metabolism of estrogens. Genetic body measurement may include GSTM1 gene that produces enzymes responsible for eliminating harmful by-products generated from metabolism of estrogens. Genetic body measurement may include GSTP1 gene that produces enzymes that eliminate harmful by-products generated from metabolism of estrogens. Genetic body measurement may include SOD2 gene that produces enzymes that eliminate oxidant by-products generated from metabolism of estrogens.

With continued reference to FIG. 1, metabolic, as used herein, includes any process that converts food and nutrition into energy. Metabolic may include biochemical processes that occur within the body. Metabolic body measurement may include blood tests, hair tests, skin tests, amniotic fluid, buccal swabs and/or tissue test to identify a user's metabolism. Metabolic body measurement may include blood tests that examine glucose levels, electrolytes, fluid balance, kidney function, and liver function. Metabolic body measurement may include blood tests that examine calcium levels, albumin, total protein, chloride levels, sodium levels, potassium levels, carbon dioxide levels, bicarbonate levels, blood urea nitrogen, creatinine, alkaline phosphatase, alanine amino transferase, aspartate amino transferase, bilirubin, and the like.

With continued reference to FIG. 1, metabolic body measurement may include one or more blood, saliva, hair, urine, skin, and/or buccal swabs that examine levels of hormones within the body such as 11-hydroxy-androsterone, 11-hydroxy-etiocholanolone, 11-keto-androsterone, 11-keto-etiocholanolone, 16 alpha-hydroxyestrone, 2-hydroxyestrone, 4-hydroxyestrone, 4-methoxyestrone, androstanediol, androsterone, creatinine, DHEA, estradiol, estriol, estrone, etiocholanolone, pregnanediol, pregnanestriol, specific gravity, testosterone, tetrahydrocortisol, tetrahydrocrotisone, tetrahydrodeoxycortisol, allo-tetrahydrocortisol.

With continued reference to FIG. 1, metabolic body measurement may include one or more metabolic rate test results such as breath tests that may analyze a user's resting metabolic rate or number of calories that a user's body burns each day rest. Metabolic body measurement may include one or more vital signs including blood pressure, breathing rate, pulse rate, temperature, and the like. Metabolic body measurement may include blood tests such as a lipid panel such as low density lipoprotein (LDL), high density lipoprotein (HDL), triglycerides, total cholesterol, ratios of lipid levels such as total cholesterol to HDL ratio, insulin sensitivity test, fasting glucose test, Hemoglobin A1C test, adipokines such as leptin and adiponectin, neuropeptides such as ghrelin, pro-inflammatory cytokines such as interleukin 6 or tumor necrosis factor alpha, anti-inflammatory cytokines such as interleukin 10, markers of antioxidant status such as oxidized low-density lipoprotein, uric acid, paraoxonase 1. Persons skilled in the art, upon reviewing the entirety of this disclosure, will be aware of various additional examples of physiological state data that may be used consistently with descriptions of systems and methods as provided in this disclosure.

With continued reference to FIG. 1, physiological data may be obtained from a physically extracted sample. A "physical sample" as used in this example, may include any sample obtained from a human body of a user. A physical sample may be obtained from a bodily fluid and/or tissue analysis such as a blood sample, tissue, sample, buccal swab, mucous sample, stool sample, hair sample, fingernail sample and the like. A physical sample may be obtained from a device in contact with a human body of a user such as a microchip embedded in a user's skin, a sensor in contact with a user's skin, a sensor located on a user's tooth, and the like. Physiological data may be obtained from a physically extracted sample. A physical sample may include a signal from a sensor configured to detect physiological data of a user and record physiological data as a function of the signal. A sensor may include any medical sensor and/or medical device configured to capture sensor data concerning a patient, including any scanning, radiological and/or imaging device such as without limitation x-ray equipment, computer assisted tomography (CAT) scan equipment, positron emission tomography (PET) scan equipment, any form of magnetic resonance imagery (MM) equipment, ultrasound equipment, optical scanning equipment such as photo-plethysmographic equipment, or the like. A sensor may include any electromagnetic sensor, including without limitation electroencephalographic sensors, magnetoencephalographic sensors, electrocardiographic sensors, electromyographic sensors, or the like. A sensor may include a temperature sensor. A sensor may include any sensor that may be included in a mobile device and/or wearable device, including without limitation a motion sensor such as an inertial measurement unit (IMU), one or more accelerometers, one or more gyroscopes, one or more magnetometers, or the like. At least a wearable and/or mobile device sensor may capture step, gait, and/or other mobility data, as well as data describing activity levels and/or physical fitness. At least a wearable and/or mobile device sensor may detect heart rate or the like. A sensor may detect any hematological parameter including blood oxygen level, pulse rate, heart rate, pulse rhythm, blood sugar, and/or blood pressure. A sensor may be configured to detect internal and/or external biomarkers and/or readings. A sensor may be a part of system 100 or may be a separate device in communication with system 100. User data may include a profile, such as a psychological profile, generated using previous item selections by the user; profile may include, without limitation, a set of actions and/or navigational actions performed as described in further detail below, which may be combined with biological extraction 112 data and/or other user data for processes such as classification to user sets as described in further detail below.

Still referring to FIG. 1, retrieval of biological extraction 112 may include, without limitation, reception of biological extraction 112 from another computing device 104 such as a device operated by a medical and/or diagnostic professional and/or entity, a user client device, and/or any device suitable for use as a third-party device as described in further detail below. Biological extraction 112 may be received via a questionnaire posted and/or displayed on a third-party device as described below, inputs to which may be processed as described in further detail below. Alternatively or additionally, biological extraction 112 may be stored in and/or retrieved from a user database 116. User database 116 may include any data structure for ordered storage and retrieval of data, which may be implemented as a hardware or software module. A user database 116 may be implemented, without limitation, as a relational database, a key-value retrieval datastore such as a NOSQL database, or any other format or structure for use as a datastore that a person skilled in the art would recognize as suitable upon review of the entirety of this disclosure. A user database 116 may include a plurality of data entries and/or records corresponding to user tests as described above. Data entries in a user database 116 may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in a user database 116 may reflect categories, cohorts, and/or populations of data consistently with this disclosure. User database 116 may be located in memory of computing device 104 and/or on another device in and/or in communication with system 100.

With continued reference to FIG. 1, and as noted above, retrieval of biological extraction may be performed multiple sequential and/or concurrent times, and any process using biological extract as described below may be performed multiple sequential and/or concurrent times; likewise, biological extract may include multiple elements of physiological data, which may be used in combination for any determination and/or other processes as described below.

With continued reference to FIG. 1, support module 108 is configured to generate a request for a user to join a support network as a function of the biological extraction 112. A "support network," as used in this disclosure, is a group of two or more users who provide one another with encouragement, comfort, and/or advice. A support network 120 may share common experiences including for example a specific medical condition or a certain stage of a disease. For example, a support network may be focused on users who have been diagnosed with an anxiety disorder, or users who have inflammatory bowel disease. A support network 120 may share common experiences, for example a support network for users who have recently experienced the death of a loved one or a support network for users who have recently suffered a traumatic event. A support network 120 may share common goals, such as a support network for users who wish to love weight or get in better physical shape. A support network 120 may share common interests, such as a support network for users who have a desire to quit smoking, or for users who have gambling addictions. A support network 120 may be composed of members who share certain characteristics and/or traits. For example, a support network 120 may be composed of members of a certain gender, members of a certain age range, members of a certain race or ethnicity, members with certain preferences, members with certain levels of activity and/or engagement of the support network 120 and the like. In an embodiment, a support network 120 includes a virtual support network. A virtual support network includes any support network that meets online. In an embodiment, a virtual support network may include in person meetings of members of a virtual support network.

With continued reference to FIG. 1, a "request to join a support network," as used in this disclosure, is data indicating a user's desire to become a member of a support network. A request to join a support network 124 may specify one or more interests and/or preferences of a support network that may be useful and/or relevant to a user. One or more elements of data pertaining to a user's preferences and inputs about a support network may be stored in user database 116. User database 116 may be implemented as any data structure as described above. Computing device 104 may receive one or more user preference 152 and/or interests in a support network from a remote device 128 operated by a user and utilizing any network methodology as described herein. A remote device 128 may include without limitation, a display in communication with computing device 104, where a display may include any display as described herein. Remote device 128 may include an additional computing device, such as a mobile device, laptop, desktop, computer and the like. Computing device 104 may receive one or more user preference 152 and/or interests in a support network entered on a graphical user interface 132 located on computing device 104. Graphical user interface 132 may include, without limitation, a form or other graphical element having display fields, where one or more elements of information may be displayed. Graphical user interface 132 may include sliders or other use inputs that may permit a user to select a particular entry. In an embodiment, a user may select one or more preferences the user has regarding support networks that may be of interest to the user. Graphical user interface 132 may include free form textual fields where a user can type in or enter one or more preferences that may be of pertinence or interest to the user.

Computing device 104 generates a request for a user to join a support network utilizing a biological extraction 112 pertaining to a user. In an embodiment, computing device 104 may consult expert database 136, to determine relevant support networks for a user. Expert database 136 may be implemented as any data structure suitable for use as user database 116 as described above. For instance and without limitation, computing device 104 may receive a biological extraction 112 pertaining to a user that contains an elevated fasting blood glucose level. In such an instance, computing device 104 may consult expert database 136 and generate a request for the user to join a support network that is focused on reducing sugar consumption in the diet, and/or a support network that is focused on increasing daily movement and/or exercise. In yet another non-limiting example, computing device 104 may receive a biological extraction 112 related to a user that contains results from a stool sample showing an altered microbial ecosystem of the user. In such an instance, computing device 104 may generate a request for the user to join a support network focused on gut health and healing.

With continued reference to FIG. 1, computing device 104 is configured to identify a support network for a user from a plurality of support networks as a function of a biological extraction 112 related to a user. Computing device 104 may identify a support network from a plurality of support networks that may align the closest with any information pertaining to the user including for example any information contained within user database 116 such as a user's biological extraction 112 and/or any preferences of the user. For instance and without limitation, computing device 104 may consult expert database 136 and create a ranked listing of support networks that may be of interest to and/or pertain to a user. Computing device 104 may then identify a support network that ranks the highest, and most closely aligns with the preferences, interests, and/or biological extraction 112 pertaining to a user.

With continued reference to FIG. 1, computing device 104 may identify a support network by classifying using a classifier and a first classification algorithm, a biological extraction to a support network. Computing device 104 generates a classifier using a classification algorithm, defined as a process whereby a computing device 104 derives, from training data, a model known as a "classifier," for sorting inputs into categories or bins of data. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. Classification may be performed utilizing inputs from expert database, as described in more detail below.

With continued reference to FIG. 1, support module 108 is configured to receive an input containing an identified self-performance target relating to a user. A "self-performance target," as used in this disclosure, is a personal goal that a user seeks to attain and/or work towards achieving. A personal goal may relate to the health, welfare, and/or well-being of the user. For example, a goal may be a desire to lose a certain amount of weight, or a desire to become more flexible. A goal may include a desire to eat less red meat, or a hope to recover from a gambling addiction. A goal may relate to a personal aspect of a user's life, such as a desire to expand the user's social network and develop new friendships. A goal may include a preference to drink no more than two glasses of wine each day, or a goal may contain a preference to get at least twenty minutes of fresh air each day. A goal may include a desire to hit a certain milestone at work or to start a new career. A goal may relate to developing a wellness practice, such as a goal to develop and practice a meditation sequence every night before bed. A goal may relate to practicing a particular form of exercise such as yoga or following a specific diet such as a diet free of grains and sugar. Computing device 104 is configured to identify a support network from a plurality of support networks using the self-performance target. Computing device 104 may identify a support network that has common performance targets to a user's self-performance target. For instance and without limitation, computing device 104 may utilize a self-performance target that contains a goal for a user to implement a daily yoga practice, to a support network that is focused on providing encouragement and support for members to develop a yoga practice. In yet another non-limiting example, computing device 104 may match a user's self-performance target to eat less red meat to a support network that focuses on meatless cooking including vegetarian and vegan options. In yet another non-limiting example, computing device 104 may match a user's self-performance target to lose weight to a support network that is focused on losing weight. In am embodiment, a self-performance target may be matched to one or more support network group improvements. For example, a self-performance target that contains a user's desire to stop drinking alcohol may be matched to a support network group improvement to stop drinking alcohol. Computing device 104 may use a self-performance target to identify a support network that is focused on one or more behaviors contained within the self-performance target. For example, a self-performance target that contains a user's desire to lose weight may be utilized to locate a support network that contains other members who are also looking to lose weight. Information relating to a user's self-performance target may be retrieved from one or more databases located within computing device 104. A self-performance target may also be utilized to organize member participants based on shared interests and shared goals as described below in more detail.

With continued reference to FIG. 1, support module 108 is configured to generate a prompt for information 140 from a user to identify the self-performance target. A "prompt for information," as used in this disclosure, any set of structured data obtained from a user. A prompt for information 140 may include a survey, interview, series of questions, reports and/or any other experience that allows a user to share data and/or information with computing device 104. In an embodiment, a prompt for information 140 may be transmitted to a remote device 128 operated by a user, where the user can respond and transmit information back to computing device 104. In yet another non-limiting example, a prompt for information 140 may be displayed on a graphical user interface 132 located on computing device 104, where a user can enter in a response. One or more responses to a prompt for information 140 may be stored within user database 116. In an embodiment, a prompt for information 140 may contain a series of questions and a series on answers that a user can choose from. In yet another non-limiting example, a prompt for information 140 may allow a user to enter in free form text any information that the user feels is pertinent.

With continued reference to FIG. 1, support module 108 identifies a support network as a function of a support network group improvement 144. A "support network group improvement," as used in this disclosure, is any achievement that a support network has achieved over a specified time period. In an embodiment, an achievement may relate to a group performance target of a support network. A "group performance target," as used in this disclosure, is any goal that a support network seeks to attain and/or work towards achieving. In an embodiment, a group performance target may mirror a self-performance target. For example, a group performance target to increase physical activity may match and be the safe as a group member's self-performance target to increase physical activity. In an embodiment, a group performance target may be related to a self-performance target. For instance and without limitation, a group performance target may describe a goal to develop an exercise routine, and a self-performance target may describe a goal to develop a specific exercise routine such as a high intensity interval training program. A group performance target may change over time as new members are added and/or removed from a virtual support network. A group performance target may also change as a goal is achieved and/or not achieved, and new goals need to be set.

With continued reference to FIG. 1, support module 108 is configured to identify a support network as a function of member engagement 148. "Member engagement," as used in this disclosure, is a measurement and/or indication of how active members are within a support network. Member engagement 148 may reflect a measurement as to participation levels of members within a support network. For instance and without limitation, a support network may have very high member engagement 148 based on factors that indicate how often members of the support network interact with one another, how frequently members of the support network are in communication with one another, how frequently members of the support network provide encouragement and support to one another, how engaged members are with achieving a group performance target, and the like. Support module 108 may identify a support network that contains a level of member engagement 148 that matches a user's preference for a certain level of member engagement 148. For example, a user may prefer to join a support network that has a very high level of member engagement 148, because the user is a very social person, and likes to have interactions with other members. In yet another non-limiting example, a user may prefer to join a support network that does not have a high level of member engagement 148 because a user has a very busy work schedule, and while the user wants to be engaged, the user does not have time for daily meetings, but only a few times each week.

With continued reference to FIG. 1, support module 108 is configured to identify a support network as a function of matching a user preference 152 to a support network preference. A "user preference," as used in this disclosure, is any selection criteria that a user has with respect to a type of online support network that a user would like to join. Selection criteria may indicate a preference for the makeup of the members of the support network. For example, selection criteria may indicate that a user would prefer to join a support network that is composed of all females who are between the ages of twenty five and thirty five. In yet another non-limiting example, selection criteria may indicate that a user would prefer to join a support network that contains members who are avid runners. Support module 108 may store one or more user preference 152 within user database 116. Support module 108 matches a user preference 152 to a support network preference. A "support network preference," as used in this disclosure, is any selection criteria that a support network has with respect to members of a support network that a support network would like to join. For example, a support network preference may highlight one or more criteria about a member that they are seeking to attain. For example, a support network may prefer a member who has a diagnosed medical condition such as irritable bowel syndrome. In yet another non-limiting example, a support network may prefer a user who has a particular problem, such as a member who has a gambling addiction or a user who is recovering from the sudden loss of a loved one. Matching may include retrieving one or more user preferences stored within user database and performing one or more machine-learning processes to assign member participants to a plurality of support networks. Matching may include for example, creating a classifier, to utilize a user preference as an input and output a support network that the user is assigned to. A classifier may include any of the classifiers as described herein. Matching may include performing one or more machine-learning processes, including any of the machine-learning processes as described herein. Support module 108 matches a user preference to a support network preference to find similar preferences and needs. For instance and without limitation, support module 108 may match a user preference 152 containing a desire to join a support network for users with stage 3 breast cancer to a support network that is for members who have breast cancer. In yet another non-limiting example, support module 108 may match a user preference 152 containing a desire to join a support network with experienced cyclists to a support network that is intended for experienced cyclists. Support module 108 may evaluate and determine how well a user is likely to fit into a support network based on how closely a user's own personal goal aligns with and/or matches a goal of other members of a support network.

With continued reference to FIG. 1, support module 108 is configured to display to a user on computing device 104 an identified support network. In an embodiment, support module 108 may display an identified support network on graphical user interface 132. In an embodiment, support module 108 may transmit an identified support network to a remote device 128 operated by a user.

With continued reference to FIG. 1, system 100 includes a machine-learning module 156 operating on computing device 104. Machine-learning module may be implemented as any hardware and/or software module. Machine-learning module 156 is configured to assess a membership of a plurality of support networks. A "membership assessment," as used in this disclosure, is any evaluation of a support network and/or individual members of a support network to identify one or more support networks and/or one or more members that need to be moved. A membership assessment may include evaluating support groups to determine support groups that are not full, and may need more members, while also evaluating support networks that have low member engagement, and could benefit from one or more members who are energetic. A membership assessment may include determining if one or more additional users need to be moved between different support networks. A membership assessment may include evaluating success rates of members of each of the plurality of support networks at achieving self-performance targets and/or group performance targets. A membership assessment may include examining how long members in a support network have been involved with the support network for, and how many group performance targets have been met over the term of a member's participation in a support network. A membership assessment include determining how active members of a support network are, and the different level of support and encouragement a support network provides to its members. For instance and without limitation, machine-learning module 156 may evaluate how much progress a support network has achieved at a group performance target such as losing weight. In such an instance, machine-learning module 156 may determine to move one or more members if members are not consistently losing weight over a given amount of time.

With continued reference to FIG. 1, machine-learning module 156 is configured to organize member participants of the plurality of support networks utilizing a first machine-learning process 160. Organizing member participants may include moving data such as such as by adding and/or subtracting members from the plurality of support networks. Organizing member participants includes moving data representing member participants to different support networks to optimize member engagement 148, member participation, and ability to assist members and/or support networks in achieving their goals.

With continued reference to FIG. 1, a "machine learning process" is a process that automatedly uses a body of data known as "training data" and/or a "training set" to generate an algorithm that will be performed by a computing device 104 and/or module to produce outputs given data provided as inputs; this is in contrast to a non-machine learning software program where the commands to be executed are determined in advance by a user and written in a programming language.

With continued reference to FIG. 1, training data," as used in this disclosure, is data containing correlations that a machine-learning process may use to model relationships between two or more categories of data elements. For instance, and without limitation, training data may include a plurality of data entries, each entry representing a set of data elements that were recorded, received, and/or generated together; data elements may be correlated by shared existence in a given data entry, by proximity in a given data entry, or the like. Multiple data entries in training data may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data according to various correlations; correlations may indicate causative and/or predictive links between categories of data elements, which may be modeled as relationships such as mathematical relationships by machine-learning processes as described in further detail below. Training data may be formatted and/or organized by categories of data elements, for instance by associating data elements with one or more descriptors corresponding to categories of data elements. As a non-limiting example, training data may include data entered in standardized forms by persons or processes, such that entry of a given data element in a given field in a form may be mapped to one or more descriptors of categories. Elements in training data may be linked to descriptors of categories by tags, tokens, or other data elements; for instance, and without limitation, training data may be provided in fixed-length formats, formats linking positions of data to categories such as comma-separated value (CSV) formats and/or self-describing formats such as extensible markup language (XML), enabling processes or devices to detect categories of data.

Alternatively or additionally, and still referring to FIG. 1, training data may include one or more elements that are not categorized; that is, training data may not be formatted or contain descriptors for some elements of data. Machine-learning algorithms and/or other processes may sort training data according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data to be made applicable for two or more distinct machine-learning algorithms as described in further detail below. Training data used by computing device 104 may correlate any input data as described in this disclosure to any output data as described in this disclosure.

Still referring to FIG. 1, selection of at least a machine-learning process may include selection of a machine-learning model, a training data set to be used in a machine-learning algorithm and/or to produce a machine-learning model, and/or a machine-learning algorithm such as lazy-learning and/or model production, or the like. Computing device 104 may be designed and configured to create a machine-learning model using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 1, machine-learning algorithms may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

Still referring to FIG. 1, models may be generated using alternative or additional artificial intelligence methods, including without limitation by creating an artificial neural network, such as a convolutional neural network comprising an input layer of nodes, one or more intermediate layers, and an output layer of nodes. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. This network may be trained using training data.

Continuing to refer to FIG. 1, machine-learning algorithms may include supervised machine-learning algorithms. Supervised machine learning algorithms, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include current membership of support networks and current group performance targets as inputs, and maximized member participation as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data. Persons skilled in the art, upon reviewing the entirety of this disclosure, will be aware of various possible variations of supervised machine learning algorithms that may be used to determine relation between inputs and outputs. Supervised machine-learning processes may include classification algorithms as defined above.

Still referring to FIG. 1, machine learning processes may include unsupervised processes. An unsupervised machine-learning process, as used herein, is a process that derives inferences in datasets without regard to labels; as a result, an unsupervised machine-learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

With continued reference to FIG. 1, machine-learning processes as described in this disclosure may be used to generate machine-learning models. A machine-learning model, as used herein, is a mathematical representation of a relationship between inputs and outputs, as generated using any machine-learning process including without limitation any process as described above, and stored in memory; an input is submitted to a machine-learning model once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model may be generated by creating an artificial neural network, such as a convolutional neural network comprising an input layer of nodes, one or more intermediate layers, and an output layer of nodes. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 1, at least a machine-learning process may include a lazy-learning process and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data. Heuristic may include selecting some number of highest-ranking associations and/or training data elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

With continued reference to FIG. 1, machine-learning module 156 is configured to organize member participants utilizing a member enhancement factor 168. A "member enhancement factor 168," as used in this disclosure, is any optimization standards that are utilized to organize memberships of support networks. Optimization standards may include improving compatibility between self-performance targets and group performance targets, user preference 152 in regards to similarities of other members contained within support networks, attributes and/or characteristics of members of support networks, participation levels among members of support networks, user satisfaction with support networks, rates of success at attaining individual and/or group goals and the like. Machine-learning module 156 may utilize one or more member enhancement factor 168 to generate a first machine-learning algorithm. For instance and without limitation, machine-learning module 156 may utilize a member enhancement factor 168 such as maximizing participation levels among members to generate a first machine-learning process 160 that utilizes current member participation to output member assignments to support networks that maximize member involvement and participation in support networks.

With continued reference to FIG. 1, support module 108 is configured to generate a machine-learning process. Support module 108 is configured to generate a diagnostic output as a function of a biological extraction 112, using a second machine-learning process 164. Support module 108 identifies a support network for a user utilizing a diagnostic output. A "diagnostic output" as used in this disclosure, is data containing a prognostic label and an ameliorative process label. A prognostic label, as described herein, is an element of data identifying and/or describing a current, incipient, or probable future medical condition affecting a person; medical condition may include a particular disease, one or more symptoms associated with a syndrome, a syndrome, and/or any other measure of current or future health and/or heathy aging. At least a prognostic label may be associated with a physical and/or somatic condition, a mental condition such as a mental illness, neurosis, or the like, or any other condition affecting human health that may be associated with one or more elements of physiological state data as described above in more detail. Conditions associated with prognostic labels may include, without limitation one or more diseases, defined for purposes herein as conditions that negatively affect structure and/or function of part or all of an organism. Conditions associated with prognostic labels may include, without limitation, acute or chronic infections, including without limitation infections by bacteria, archaea, viruses, viroids, prions, single-celled eukaryotic organisms such as amoeba, paramecia, trypanosomes, plasmodia, *leishmania*, and/or fungi, and/or multicellular parasites such as nematodes, arthropods, fungi, or the like. Prognostic labels may be associated with one or more immune disorders, including without limitation immunodeficiencies and/or auto-immune conditions. Prognostic labels may be associated with one or more metabolic disorders. Prognostic labels may be associated with one or more endocrinal disorders. Prognostic labels may be associated with one or more cardiovascular disorders. Prognostic labels may be associated with one or more respiratory disorders. Prognostic labels may be associated with one or more disorders affecting connective tissue. Prognostic labels may be associated with one or more digestive disorders. Prognostic labels may be associated with one or more neurological disorders such as neuromuscular disorders, dementia, or the like. Prognostic labels may be associated with one or more disorders of the excretory system, including without limitation nephrological disorders. Prognostic labels may be associated with one or more liver disorders. Prognostic labels may be associated with one or more disorders of the bones such as osteoporosis. Prognostic labels may be associated with one or more disorders affecting joints, such as osteoarthritis, gout, and/or rheumatoid arthritis. Prognostic labels be associated with one or more cancers, including without limitation carcinomas, lymphomas, leukemias, germ cell tumor cancers, blastomas, and/or sarcomas. Prognostic labels may include descriptors of latent, dormant, and/or apparent disorders, diseases, and/or conditions. Prognostic labels may include descriptors of conditions for which a person may have a higher than average probability of development, such as a condition for which a person may have a "risk factor"; for instance, a person currently suffering from abdominal obesity may have a higher than average probability of developing type II diabetes. The above-described examples are presented for illustrative purposes only and are not intended to be exhaustive. Persons skilled in the art, upon reviewing the entirety of this disclosure, will be aware of various additional examples of conditions that may be associated with prognostic labels as described in this disclosure. An ameliorative process label may contain therapies, treatments, and/or lifestyle or dietary choices that may alleviate conditions associated with prognostic labels. Computing device 104 generates a diagnostic output by identifying, a current condition of the user utilizing a first training set, said first training set including a plurality of data entries, each first data entry of the plurality of data entries including an element of physiological state data and a correlated first prognostic label. Computing device 104 identifies, an ameliorative output related to the current condition of the user as a function of the identified current condition of the user and a second training set, said second training set including a plurality of second data entries, each second data entry including a second prognostic label and a correlated ameliorative process label. Training data includes any of the training data as described herein. A second machine-learning process includes any of the machine-learning processes suitable for use as first machine-learning process 160 as described above in more detail.

With continued reference to FIG. 1, machine-learning module 156 is configured to select a support network leader 172 contained within an identified support network. A "support network leader," as used in this disclosure, is a group manager who is responsible for organizing a support network. A support network leader 172 may help administer a support network, set meeting times for a support network, and be in charge of a support network. A support network leader 172 may be selected by a member selection process. A "member selection process," as used in this disclosure is any election process of a member of a support network to become a support network leader 172. An election process may include a formal voting process, where members of a support network may vote to elect one member of a support network to become a support network leader 172. In yet another non-limiting example, an election process may include a nomination process of a member to become a support network leader 172 based on a member's performance such as how engaged a member is, how well a member has achieved any self-performance targets and the like. In an embodiment, an election process may include a nomination process where one or more members may nominate a member of a support network to become a support network leader 172. In an embodiment, machine-learning module 156 may select a member to become a support network leader 172 when there are no nominations, or there is a dispute about who should become a support network leader 172.

Figure 2:
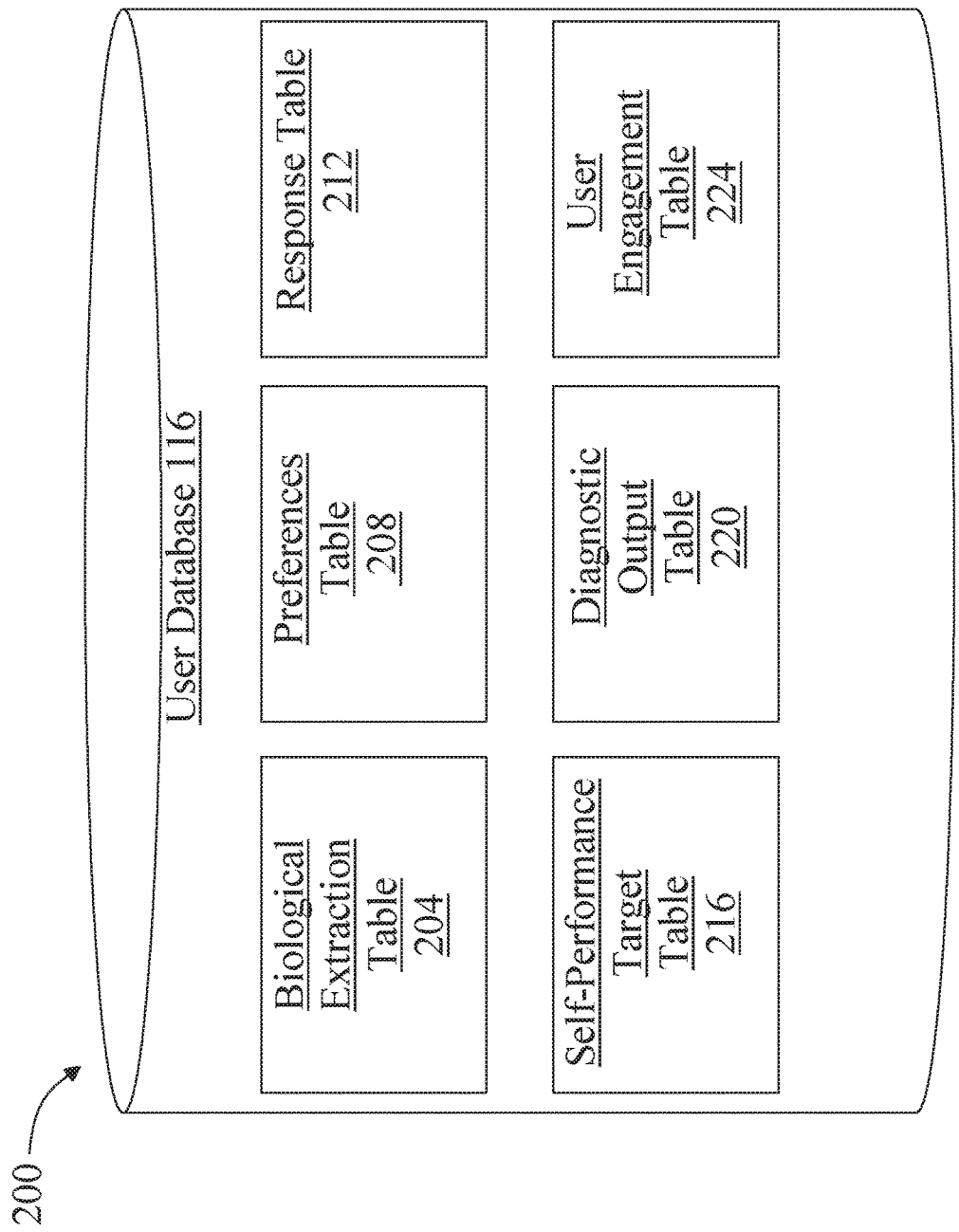
FIG. 2 is a block diagram illustrating an exemplary embodiment of a user database.

Referring now to FIG. 2, an exemplary embodiment 200 of user database 116 is illustrated. User database 116 may be implemented as any data structure as described above in more detail in reference to FIG. 1. One or more tables contained within user database 116 may include biological extraction table 204; biological extraction table 204 may include one or more biological extractions 112 pertaining to a user. For instance and without limitation, biological extraction table 204 may include results from a stool sample analyzed for the presence and/or absence of certain strains of bacteria. One or more tables contained within user database 116 may include preferences table 208; preferences table 208 may include one or more user preference 152 regarding a support network. For instance and without limitation, preferences table 208 may include user input describing a user's preference to join a support network that has members who are between the ages of forty and fifty five, and who are high involved with a support network. One or more tables contained within user database 116 may include response table 212; response table 212 may include any user responses generated in response to a prompt for information 140. For instance and without limitation, response table 212 may include a user response that details a user's personal health goal to lose fifteen pounds of body weight. One or more tables contained within user database 116 may include self-performance target table 216; self-performance target table 216 may include one or more user self-performance targets. For instance and without limitation, self-performance target table 216 may include a user's self-performance target to develop a daily meditation practice. One or more tables contained within user database 116 may include diagnostic output table 220; diagnostic output table 220 may contain one or more diagnoses of the user. For instance and without limitation, diagnostic output table 220 may contain a diagnosis of allergic rhinitis generated utilizing a machine-learning process as described above in more detail in reference to FIG. 1. One or more tables contained within user database 116 may include user engagement table 224; user engagement table 224 may include data describing a user's engagement with system 100. For instance and without limitation, user engagement table 224 may describe how many times a user interacted with a support network over a certain amount of time.

Figure 3:
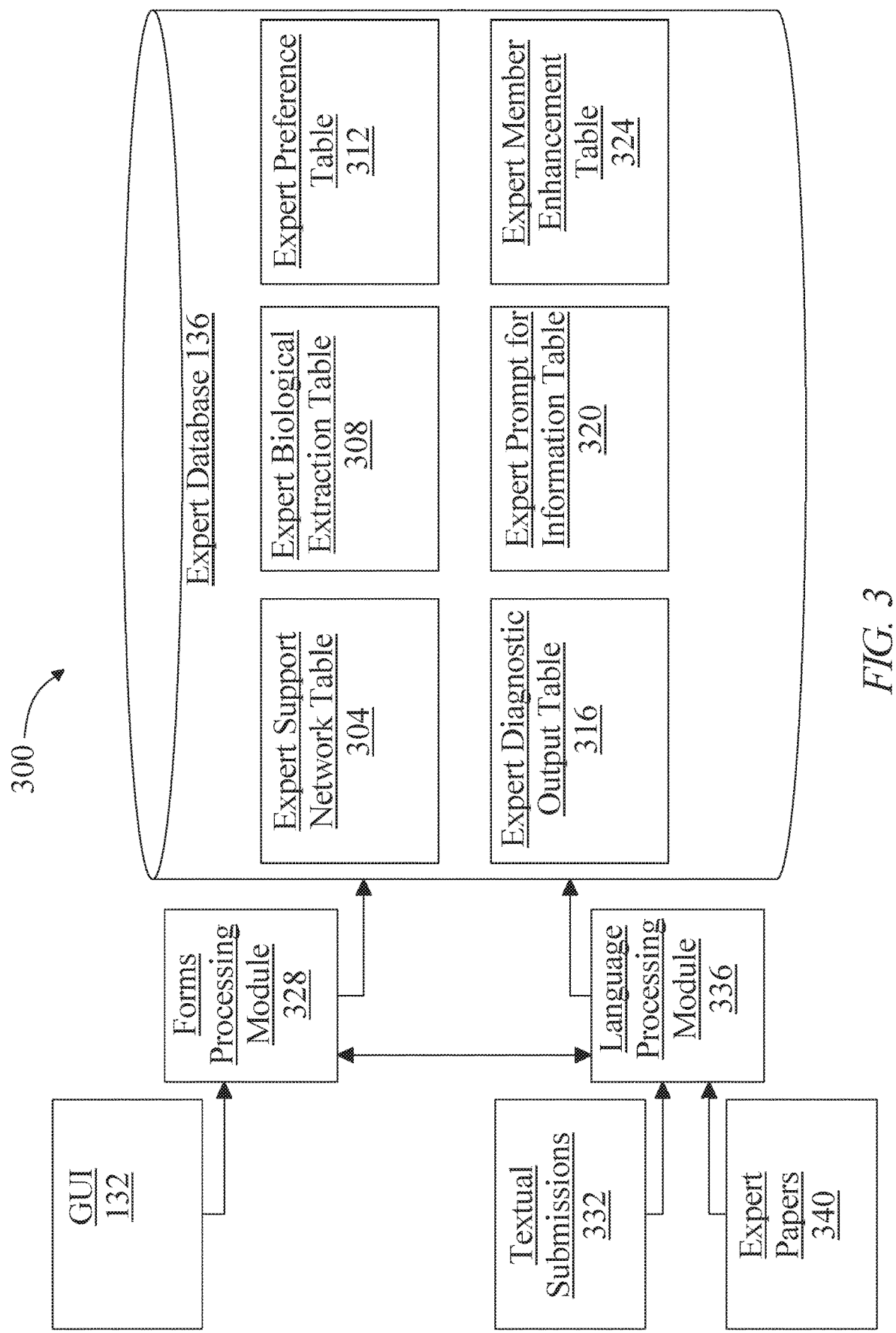
FIG. 3 is a block diagram illustrating an exemplary embodiment of an expert database.

Referring now to FIG. 3, an exemplary embodiment 300 of expert database 136 is illustrated. Expert database 136 may, as a non-limiting example, organize data stored in the expert database 136 according to one or more database tables. One or more database tables may be linked to one another by, for instance, common column values. For instance, a common column between two tables of expert database 136 may include an identifier of an expert submission, such as a form entry, textual submission, expert paper, or the like, for instance as defined below; as a result, a query may be able to retrieve all rows from any table pertaining to a given submission or set thereof. Other columns may include any other category usable for organization or subdivision of expert data, including types of expert data, names and/or identifiers of experts submitting the data, times of submission, or the like; persons skilled in the art, upon reviewing the entirety of this disclosure, will be aware of various ways in which expert data from one or more tables may be linked and/or related to expert data in one or more other tables.

Still referring to FIG. 3, one or more database tables in expert database 136 may include, as a non-limiting example, an expert support network table 304; an expert support network table 304 may include expert information relating to support networks. One or more database tables in expert database 136 may include, as a non-limiting example, an expert biological extraction table 308; expert biological extraction table 308 may include expert information relating to biological extractions 112. One or more database tables in expert database 136 may include, expert preference table 312; expert preference table 312 may include expert information relating to user and/or support network preferences. One or more database tables in expert database 136 may include, expert diagnostic output table 316; expert diagnostic output table 316 may include expert information relating to diagnostic outputs. One or more database tables in expert database 136 may include, expert prompt for information table 320; expert prompt for information table 320 may include expert information relating to prompts for information. One or more database tables in expert database 136 may include expert member enhancement table 324; expert member enhancement table 324 may include expert information relating to member enhancement factor 168.

In an embodiment, and still referring to FIG. 3, a forms processing module 328 may sort data entered in a submission via a graphical user interface 132 receiving expert submissions by, for instance, sorting data from entries in the graphical user interface 132 to related categories of data; for instance, data entered in an entry relating in the graphical user interface 132 to a biological extraction 112, which may be provided to expert biological extraction table 308, while data entered in an entry relating to member enhancement factors 168, which may be provided to expert member enhancement table 324. Where data is chosen by an expert from pre-selected entries such as drop-down lists, data may be stored directly; where data is entered in textual form, a language processing module may be used to map data to an appropriate existing label, for instance using a vector similarity test or other synonym-sensitive language processing test to map data to existing labels and/or categories. Similarly, data from an expert textual submission 332, such as accomplished by filling out a paper or PDF form and/or submitting narrative information, may likewise be processed using language processing module.

Still referring to FIG. 3, a language processing module 336 may include any hardware and/or software module. Language processing module 336 may be configured to extract, from the one or more documents, one or more words. One or more words may include, without limitation, strings of one or characters, including without limitation any sequence or sequences of letters, numbers, punctuation, diacritic marks, engineering symbols, geometric dimensioning and tolerancing (GD&T) symbols, chemical symbols and formulas, spaces, whitespace, and other symbols, including any symbols usable as textual data as described above. Textual data may be parsed into tokens, which may include a simple word (sequence of letters separated by whitespace) or more generally a sequence of characters as described previously. The term "token," as used herein, refers to any smaller, individual groupings of text from a larger source of text; tokens may be broken up by word, pair of words, sentence, or other delimitation. These tokens may in turn be parsed in various ways. Textual data may be parsed into words or sequences of words, which may be considered words as well. Textual data may be parsed into "n-grams", where all sequences of n consecutive characters are considered. Any or all possible sequences of tokens or words may be stored as "chains", for example for use as a Markov chain or Hidden Markov Model.

Still referring to FIG. 3 language processing module 336 may compare extracted words to categories of data to be analyzed; such data for comparison may be entered on computing device 104 as described above using expert data inputs or the like. In an embodiment, one or more categories may be enumerated, to find total count of mentions in such documents. Alternatively or additionally, language processing module 336 may operate to produce a language processing model. Language processing model may include a program automatically generated by at least a server and/or language processing module 336 to produce associations between one or more words extracted from at least a document and detect associations, including without limitation mathematical associations, between such words, and/or associations between such words and other elements of data analyzed, processed and/or stored by system 100. Associations between language elements, may include, without limitation, mathematical associations, including without limitation statistical correlations between any language element and any other language element and/or language elements. Statistical correlations and/or mathematical associations may include probabilistic formulas or relationships indicating, for instance, a likelihood that a given extracted word indicates a given category of physiological data, a given relationship of such categories to prognostic labels, and/or a given category of prognostic labels. As a further example, statistical correlations and/or mathematical associations may include probabilistic formulas or relationships indicating a positive and/or negative association between at least an extracted word and/or a given category of data; positive or negative indication may include an indication that a given document is or is not indicating a category of data.

Still referring to FIG. 3, language processing module 336 and/or computing device 104 may generate the language processing model by any suitable method, including without limitation a natural language processing classification algorithm; language processing model may include a natural language process classification model that enumerates and/or derives statistical relationships between input term and output terms. Algorithm to generate language processing model may include a stochastic gradient descent algorithm, which may include a method that iteratively optimizes an objective function, such as an objective function representing a statistical estimation of relationships between terms, including relationships between input terms and output terms, in the form of a sum of relationships to be estimated. In an alternative or additional approach, sequential tokens may be modeled as chains, serving as the observations in a Hidden Markov Model (HMM). HMMs as used herein are statistical models with inference algorithms that that may be applied to the models. In such models, a hidden state to be estimated may include an association between an extracted word category of physiological data, a given relationship of such categories to prognostic labels, and/or a given category of prognostic labels. There may be a finite number of category of physiological data, a given relationship of such categories to prognostic labels, and/or a given category of prognostic labels to which an extracted word may pertain; an HMM inference algorithm, such as the forward-backward algorithm or the Viterbi algorithm, may be used to estimate the most likely discrete state given a word or sequence of words. Language processing module 336 may combine two or more approaches. For instance, and without limitation, machine-learning program may use a combination of Naive-Bayes (NB), Stochastic Gradient Descent (SGD), and parameter grid-searching classification techniques; the result may include a classification algorithm 132 that returns ranked associations.

Continuing to refer to FIG. 3, generating language processing model may include generating a vector space, which may be a collection of vectors, defined as a set of mathematical objects that can be added together under an operation of addition following properties of associativity, commutativity, existence of an identity element, and existence of an inverse element for each vector, and can be multiplied by scalar values under an operation of scalar multiplication compatible with field multiplication, and that has an identity element is distributive with respect to vector addition, and is distributive with respect to field addition. Each vector in an n-dimensional vector space may be represented by an n-tuple of numerical values. Each unique extracted word and/or language element as described above may be represented by a vector of the vector space. In an embodiment, each unique extracted and/or other language element may be represented by a dimension of vector space; as a non-limiting example, each element of a vector may include a number representing an enumeration of co-occurrences of the word and/or language element represented by the vector with another word and/or language element. Vectors may be normalized, scaled according to relative frequencies of appearance and/or file sizes. In an embodiment associating language elements to one another as described above may include computing a degree of vector similarity between a vector representing each language element and a vector representing another language element; vector similarity may be measured according to any norm for proximity and/or similarity of two vectors, including without limitation cosine similarity, which measures the similarity of two vectors by evaluating the cosine of the angle between the vectors, which can be computed using a dot product of the two vectors divided by the lengths of the two vectors. Degree of similarity may include any other geometric measure of distance between vectors.

Still referring to FIG. 3, language processing module 336 may use a corpus of documents to generate associations between language elements in a language processing module 336, and computing device 104 may then use such associations to analyze words extracted from one or more documents. Documents may be entered into computing device 104 by being uploaded by an expert or other persons using, without limitation, file transfer protocol (FTP) or other suitable methods for transmission and/or upload of documents; alternatively or additionally, where a document is identified by a citation, a uniform resource identifier (URI), uniform resource locator (URL) or other datum permitting unambiguous identification of the document, computing device 104 may automatically obtain the document using such an identifier, for instance by submitting a request to a database or compendium of documents such as JSTOR as provided by Ithaka Harbors, Inc. of New York.

With continued reference to FIG. 3, data may be extracted from expert papers 340, which may include without limitation publications in medical and/or scientific journals, by language processing module 336 via any suitable process as described herein. Persons skilled in the art, upon reviewing the entirety of this disclosure, will be aware of various additional methods whereby novel terms may be separated from already-classified terms and/or synonyms therefore, as consistent with this disclosure.

Figure 4:
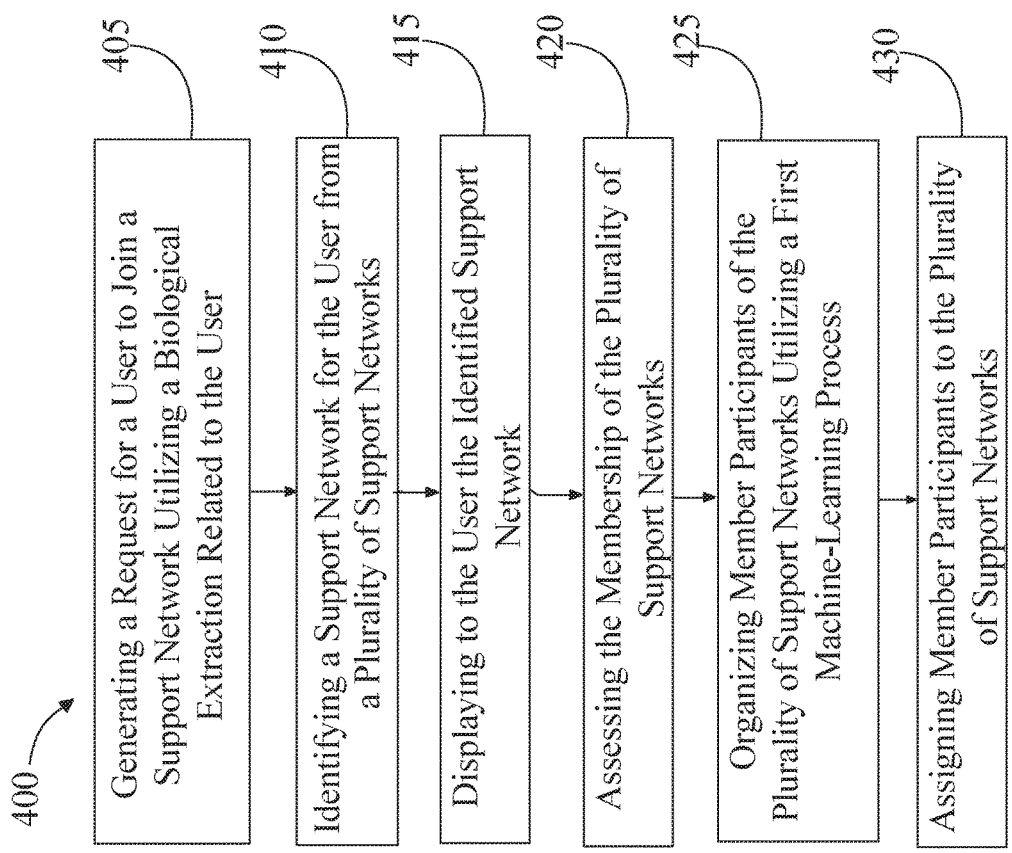
FIG. 4 is a process flow diagram illustrating an exemplary embodiment of a method of a physiologically informed virtual support network.

Referring now to FIG. 4, an exemplary embodiment 400 of a method of a physiologically informed virtual support network is illustrated. At step 405, computing device 104 generates a request for a user to join a support network utilizing a biological extraction 112 related to the user. A support network includes any of the support networks as described above in more detail in reference to FIG. 1. In an embodiment, a support network may be intended to help provide support and motivation to a user from other members of the support network. Members of a support network may have experienced common life events and/or shared experiences. For example, a support network may be composed of members who have suffered a traumatic event. In yet another non-limiting example, a support network may be composed of members who are all within a certain age range. A biological extraction 112 includes any of the biological extraction 112 as described above in more detail in reference to FIG. 1. For instance and without limitation, a biological extraction 112 may include a saliva sample analyzed for one or more genetic variants. In yet another non-limiting example, a biological extraction 112 may include a stool sample analyzed for one or more markers of toxicity within the body such as lead, mercury, mold, and fungus. Computing device 104 utilizes a biological extraction 112 pertaining to a user to generate a request for a user to join a support network. Computing device 104 may consult expert database 136 to determine types of support networks that may be of interest to the user based on the user's biological extraction 112. For instance and without limitation, computing device 104 may consult expert database 136 to determine that a biological extraction 112 such as a stool sample showing a high level of *Candida albicans* may be best suited for support networks composed of other members who also have high levels of *Candida albicans* in the body. In yet another non-limiting example, computing device 104 may consult expert database 136 to determine that a biological extraction 112 reflecting a user has high blood lipids and high blood sugar may be best suited for a support network that is focused on increasing member fitness and activity level.

With continued reference to FIG. 4, at step 410 computing device 104 identifies a support network for a user from a plurality of support networks as a function of a biological extraction 112 pertaining to a user. Computing device 104 identifies support networks that may contain members that have similar biological extraction 112, and/or support networks that may be of interest to a user with a particular biological extraction 112. Computing device 104 identifies support networks by consulting expert database 136. Computing device 104 receives an input containing a self-performance target relating to a user. A self-performance target includes any of the self-performance targets as described above in more detail in reference to FIG. 1. For instance and without limitation, a self-performance target may describe a personal goal that a user seeks to attain and/or work towards achieving. A self-performance target may relate to the health, welfare, and/or well-being of a user. For example, a self-performance target may contain a user's goal to lose a certain percentage of body fat. In yet another non-limiting example, a self-performance target may contain a user's goal to become a blue belt at karate. Computing device 104 may receive an input containing a self-performance target from a user from remote device 128 which may be operated by the user. In yet another non-limiting example, computing device 104 may receive an input containing a self-performance target entered by a user on graphical user interface 132 located on computing device 104. Graphical user interface 132 includes any of the graphical user interface 132 as described above in more detail. Computing device 104 receives an input containing a self-performance target utilizing any network methodology as described herein. Computing device 104 identifies a support network from a plurality of support networks utilizing a self-performance target. For example, computing device 104 may utilize a self-performance target to identify support networks that have members with similar self-performance targets, and/or support networks that may be of interest to a user with a particular self-performance target. For instance and without limitation, computing device 104 may identify a support network that has other members who are interested in cooking vegetarian meals at home for a user with a self-performance target to implement a vegetarian diet. Computing device 104 generates a prompt for information 140 from a user to identify a self-performance target. A prompt for information 140 includes any of the prompts for information as described above in more detail in reference to FIG. 1. In an embodiment, a prompt for information 140 contains a questionnaire. A questionnaire includes any of the questionnaires as described above in reference to FIG. 1.

With continued reference to FIG. 4, computing device 104 is configured to generate a diagnostic output as a function of a biological extraction 112 using a second machine-learning process. Diagnostic output includes any of the diagnostic outputs as described above in more detail in reference to FIG. 1. Diagnostic output is generated using a second machine-learning process, as described above in more detail in reference to FIG. 1. Computing device 104 utilizes a diagnostic output to identify a support network for a user. For instance and without limitation, computing device 104 may utilize a diagnostic output to identify support networks that have members who have the same or similar diagnostic output to the user. For instance and without limitation, computing device 104 may use a user's diagnostic output that indicates the user has rheumatoid arthritis to locate a support network that contains members who also have rheumatoid arthritis. In yet another non-limiting example, computing device 104 may utilize an ameliorative label contained within a diagnostic output to locate other support networks that have users with the same recommended ameliorative labels. For example, an ameliorative label may indicate that a user is recommended to develop a meditation practice, and computing device 104 may locate support networks that are intended to help members develop meditation practices. In an embodiment, a diagnostic output may be utilized to organize member participants contained within a plurality of support networks. Computing device 104 may utilize a diagnostic output and one or more machine-learning processes to identify a support network for a user. A machine-learning process may include any of the machine-learning processes as described herein. For example, computing device 104 may generate a classifier, and utilize a diagnostic output as an input to the classifier, and output identified support networks.

With continued reference to FIG. 4, computing device 104 identifies support networks based on information provided about various support networks. Computing device 104 identifies support networks based on a support network group improvement 144. A support network group improvement 144 includes any achievement that a support network has achieved over a specified time period. For example, a support network group improvement 144 may indicate that a support network lost a collective of fifty pounds over a total of six months. In yet another non-limiting example, a support network group improvement 144 may indicate that all members of a support network practiced a meditation sequence three nights every week for the past six weeks.

Computing device 104 identifies a support network based on member engagement 148. Computing device 104 may evaluate a user's preference to determine how engaged a user prefers to be with a support network. Computing device 104 may identify support networks that have similar member engagement 148 to the amount of engagement that a user seeks a support network to have. Computing device 104 may collect information about a user's preferences in regard to a support network and store the information within user database 116. Computing device 104 matches a user preference 152 to a support network preference. Matching may include determining how closely a user's preferences align with a support network's preferences. For instance and without limitation, a user may prefer a support network that has members who are highly engaged and constantly achieving group performance targets. In such an instance, computing device 104 matches the user preference 152 to support networks that are also seeking highly engaged members to join a particular support network.

With continued reference to FIG. 4, at step 415, computing device 104 displays to a user on computing device 104 an identified support network. Computing device 104 displays an identified support network utilizing any methodology as described herein. For instance and without limitation, computing device 104 may display an identified support network on a graphical user interface 132 located on computing device 104.

Figure 5:
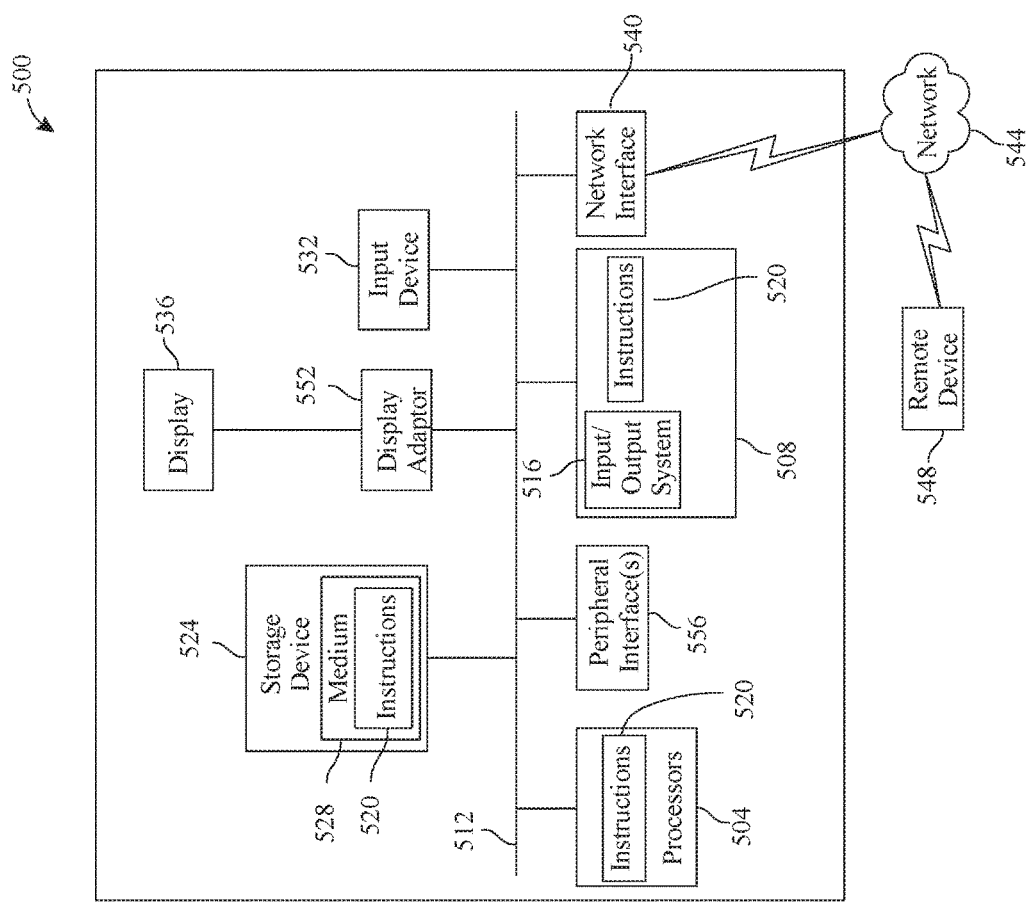
FIG. 5 is a block diagram of a computing system that can be used to implement any one or more of the methodologies disclosed herein and any one or more portions thereof.

With continued reference to FIG. 5, at step 420, computing device 104 assesses membership of a plurality of support networks. Computing device 104 assess a plurality of support networks to determine if members need to be moved to other support networks based on metrics such as member engagement 148 as well as a support network group improvement 144. Computing device 104 may consult expert database 136 to determine success rates of what member engagement 148 and support network group improvement 144 numbers should reflect. For example, computing device 104 may determine that members of a support network that has chronically low member engagement 148 needs to have its members reassigned to other support networks that have consistently higher levels of member engagement 148. In yet another non-limiting example, computing device 104 may determine that support networks that have not achieved any support network group improvement 144 may need to have new members assigned to the support network to help motive and encourage existing members to achieve a support network group improvement 144.

With continued reference to FIG. 4, at step 425, computing device 104 organizes member participants of a plurality of support networks utilizing a first machine-learning process 160. A first machine-learning process includes any of the machine-learning processes as descried above in more detail in reference to FIG. 1. Computing device 104 utilizes a first machine-learning process 160 to optimize members contained within each of a plurality of support networks. Computing device 104 may optimize members utilizing a member enhancement factor 168. A member enhancement factor 168 includes any of the member enhancement factor 168 as described above in more detail in reference to FIG. 1. Computing device 104 may optimize a first machine-learning process by retrieving a member enhancement factor based on inputs contained within expert database 136. Computing device 104 may organize member participants based on member enhancement factor 168 that seek to improve compatibilities between users and other members of support networks, participation levels of members, overall success of support networks at achieving goals and the like.

With continued reference to FIG. 4, at step 430, computing device 104 assigns member participants to a plurality of support networks as a function of a first machine-learning process 160. Assigning member participants includes moving one or more members between a plurality of support networks based on a first machine-learning process 160. Members may be moved based on determinations as to how support networks can be best optimized based on user compatibility with other members of support networks, participation levels of members of support networks, identification of support network leader 172, and the like. Computing device 104 assigns participants to a plurality of support networks based on identifying a support network leader 172. A support network leader 172 includes any of the support network leader 172 as described above in more detail in reference to FIG. 1. A support network leader 172 may be identified by a member selection process. A member selection process includes any of the member selection processes as described above in more detail in reference to FIG. 1.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

FIG. 5 shows a diagrammatic representation of one embodiment of a computing device in the exemplary form of a computer system 500 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 500 includes a processor 504 and a memory 508 that communicate with each other, and with other components, via a bus 512. Bus 512 may include any of several types of bus structures including, but not limited to, a memory bus, a memory controller, a peripheral bus, a local bus, and any combinations thereof, using any of a variety of bus architectures.

Memory 508 may include various components (e.g., machine-readable media) including, but not limited to, a random access memory component, a read only component, and any combinations thereof. In one example, a basic input/output system 516 (BIOS), including basic routines that help to transfer information between elements within computer system 500, such as during start-up, may be stored in memory 508. Memory 508 may also include (e.g., stored on one or more machine-readable media) instructions (e.g., software) 520 embodying any one or more of the aspects and/or methodologies of the present disclosure. In another example, memory 508 may further include any number of program modules including, but not limited to, an operating system, one or more application programs, other program modules, program data, and any combinations thereof.

Computer system 500 may also include a storage device 524. Examples of a storage device (e.g., storage device 524) include, but are not limited to, a hard disk drive, a magnetic disk drive, an optical disc drive in combination with an optical medium, a solid-state memory device, and any combinations thereof. Storage device 524 may be connected to bus 512 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 524 (or one or more components thereof) may be removably interfaced with computer system 500 (e.g., via an external port connector (not shown)). Particularly, storage device 524 and an associated machine-readable medium 528 may provide nonvolatile and/or volatile storage of machine-readable instructions, data structures, program modules, and/or other data for computer system 500. In one example, software 520 may reside, completely or partially, within machine-readable medium 528. In another example, software 520 may reside, completely or partially, within processor 504.

Computer system 500 may also include an input device 532. In one example, a user of computer system 500 may enter commands and/or other information into computer system 500 via input device 532. Examples of an input device 532 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 532 may be interfaced to bus 512 via any of a variety of interfaces (not shown) including, but not limited to, a serial interface, a parallel interface, a game port, a USB interface, a FIREWIRE interface, a direct interface to bus 512, and any combinations thereof. Input device 532 may include a touch screen interface that may be a part of or separate from display 536, discussed further below. Input device 532 may be utilized as a user selection device for selecting one or more graphical representations in a graphical interface as described above.

A user may also input commands and/or other information to computer system 500 via storage device 524 (e.g., a removable disk drive, a flash drive, etc.) and/or network interface device 540. A network interface device, such as network interface device 540, may be utilized for connecting computer system 500 to one or more of a variety of networks, such as network 544, and one or more remote devices 548 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 544, may employ a wired and/or a wireless mode of communication. In general, any network topology may be used. Information (e.g., data, software 520, etc.) may be communicated to and/or from computer system 500 via network interface device 540.

Computer system 500 may further include a video display adapter 552 for communicating a displayable image to a display device, such as display device 536. Examples of a display device include, but are not limited to, a liquid crystal display (LCD), a cathode ray tube (CRT), a plasma display, a light emitting diode (LED) display, and any combinations thereof. Display adapter 552 and display device 536 may be utilized in combination with processor 504 to provide graphical representations of aspects of the present disclosure. In addition to a display device, computer system 500 may include one or more other peripheral output devices including, but not limited to, an audio speaker, a printer, and any combinations thereof. Such peripheral output devices may be connected to bus 512 via a peripheral interface 556. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for a physiologically informed virtual support network, the system comprising:
   a computing device, wherein the computing device is configured to:
      perform a psychological assessment and a cognitive assessment of a user;
      generate user physiological data as a function of the psychological assessment and the cognitive assessment;
   a support module operating on the computing device, the support module configured to:
   receive a biological extraction related to a user, wherein the biological extraction comprises an element of the user physiological data;
   receive at least a user preference from a remote device;
   generate a request for the user to join a support network as a function of the biological extraction;
   identify a support network for the user from a plurality of support networks, as a function of the biological extraction, the identifying of the support network comprising:
      creating support network training data using data from an expert database correlating expert biological extraction table data to expert support network table data; generating, by the computing device, a support network classifier using the support network training data;
      matching, using a support network preference classifier, the at least a user preference and at least a support network preference, wherein the matching is performed as a function of a diagnosed medical condition of the user; and
      identifying the support network for the user using the support network classifier and the biological extraction in combination with the matching between the at least a user preference and the at least a support network preference; and
   display to the user on the computing device, the identified support network; and
   a machine-learning module operating on the computing device, the machine-learning module configured to:
   assess a membership of the plurality of support networks;
   organize member participants of the plurality of support networks utilizing a first machine-learning process generated based on a member enhancement factor, wherein the member enhancement factor comprises similarities between the at least a user preference and members of support networks; and
   assign member participants to the plurality of support networks as a function of the first machine-learning process.

2. The system of claim 1, wherein the support module is further configured to: receive an input containing a self-performance target relating to the user; and identify the support network from the plurality of support networks using the self-performance target.

3. The system of claim 2, wherein the support module is further configured to: generate a prompt for information from the user to identify the self-performance target, wherein the prompt for information further comprises a questionnaire.

4. The system of claim 1, wherein the support module is further configured to: generate a diagnostic output as a function of the biological extraction, using a second machine-learning process; and identify the support network for the user as a function of the diagnostic output.

5. The system of claim 1, wherein the support module is further configured to identify the support network as a function of a support network group improvement.

6. The system of claim 1, wherein the support module is further configured to identify the support network as a function of member engagement.

7. The system of claim 1, wherein the machine-learning module is further configured to: select a support network leader contained within the identified support network.

8. The system of claim 1, wherein the machine-learning module is further configured to organize member participants using a classification algorithm.

9. The system of claim 1, wherein the machine-learning module is further configured to organize member participants utilizing the member enhancement factor.

10. The system of claim 1, wherein the diagnosed medical condition of the user comprises a gambling addiction.

11. A method of a physiologically informed virtual support network, the method comprising:
   performing, by a computing device, a psychological assessment and a cognitive assessment of a user;
   generating, by the computing device, user physiological data as a function of psychological assessment and the cognitive assessment;
   receiving, by the computing device, at least a user preference from a remote device;
   generating, by the computing device, a request for a user to join a support network as a function of a biological extraction related to a user, wherein the biological extraction comprises an element of user physiological data;
   identifying, by the computing device, a support network for the user from a plurality of support networks, as a function of the biological extraction, the identifying the support network comprising:
      creating support network training data using data from an expert database correlating expert biological extraction table data to expert support network table data;
      generating, by the computing device, a support network classifier using the support network training data; and
      matching, using a support network preference classifier, the at least a user preference and at least a support network preference, wherein the matching is performed as a function of a diagnosed medical condition of the user; and identifying the support network for the user using the support network classifier and the biological extraction in combination with the matching between the at least a user preference and the at least a support network preference;

displaying, to the user and on the computing device, the identified support network;

assessing, by the computing device, a membership of the plurality of support networks;

organizing, by the computing device, the membership of the plurality of support networks utilizing a first machine-learning process, the first machine learning process generated based on a member enhancement factor, wherein the member enhancement factor comprises similarities between the at least a user preference and members of support networks; and assigning, by the computing device, the membership to the plurality of support networks as a function of the first machine-learning process.

12. The method of claim 11, wherein identifying the support network further comprises: receiving an input containing a self-performance target relating to the user; and identifying the support network from the plurality of support networks using the self-performance target.

13. The method of claim 12, wherein receiving the input further comprises: generating a prompt for information from the user to identify the self-performance target, wherein the prompt for information further comprises a questionnaire.

14. The method of claim 11, wherein identifying the support network further comprises: generating a diagnostic output as a function of the biological extraction, using a second machine-learning process; and identifying the support network for the user as a function of the diagnostic output.

15. The method of claim 11, wherein identifying the support network further comprises identifying the support network as a function of a support network group improvement.

16. The method of claim 11, wherein identifying the support network further comprises identifying the support network as a function of member engagement.

17. The method of claim 11, wherein organizing the membership of the plurality of support networks further comprises selecting a support network leader contained within the identified support network.

18. The method of claim 11, wherein organizing the membership of the plurality of support networks further comprises generating a classification algorithm.

19. The method of claim 11, wherein organizing the membership of the plurality of support networks further comprises organizing member participants utilizing the member enhancement factor.

20. The method of claim 11, wherein the matching is performed as a function of a dimension of the user's body, wherein the dimension of the user's body comprises an epigenetic body measurement, a microbiome body measurement or a genetic body measurement.

* * * * *